United States Patent [19]

Sagisaka et al.

[11] Patent Number: 6,009,866
[45] Date of Patent: Jan. 4, 2000

[54] OXYGEN CONCENTRATION DETECTING APPARATUS

[75] Inventors: Yasuo Sagisaka, Komaki; Yukihiro Yamashita, Kariya, both of Japan

[73] Assignee: Nippondenso Co., Ltd., Kariya, Japan

[21] Appl. No.: 08/988,358

[22] Filed: Dec. 10, 1997

Related U.S. Application Data

[62] Division of application No. 08/621,692, Mar. 26, 1996, Pat. No. 5,709,198.

[30] Foreign Application Priority Data

Mar. 31, 1995 [JP] Japan ......................... 7-76338

[51] Int. Cl.[7] .................................................. F02D 41/22
[52] U.S. Cl. ........................ 123/681; 123/685; 123/687; 123/690; 123/697; 73/118.1
[58] Field of Search ..................................... 123/681, 685, 123/687, 688, 690, 697; 73/118.1; 204/401

[56] References Cited

U.S. PATENT DOCUMENTS

| | | | |
|---|---|---|---|
| 4,732,128 | 3/1988 | Yoshioka et al. | 123/697 |
| 5,090,387 | 2/1992 | Mayer et al. | 123/688 |
| 5,148,795 | 9/1992 | Nagai et al. | 123/697 |
| 5,214,267 | 5/1993 | Hoshi et al. | 219/497 |
| 5,719,778 | 2/1998 | Suzumura et al. | 364/477.01 |

FOREIGN PATENT DOCUMENTS

| | | |
|---|---|---|
| 1-232143 | 9/1989 | Japan. |
| 3-189350 | 8/1991 | Japan. |
| 4-69565 | 3/1992 | Japan. |

Primary Examiner—Tony M. Argenbright
Assistant Examiner—Arnold Castro
Attorney, Agent, or Firm—Pillsbury Madison & Sutro

[57] ABSTRACT

An oxygen concentration detecting apparatus precisely and easily performs diagnosis of a limit current type oxygen sensor. The limit current type oxygen sensor has an oxygen concentration detecting element for outputting limit current proportional to the oxygen concentration and a heater for heating the detecting element. A CPU of a microcomputer controls energization of the heater to activate the oxygen sensor. The CPU calculates element resistance based on the voltage applied to the oxygen sensor and the current detected in the sensor. In a sensor diagnosis routine, the CPU determines whether preconditions for the diagnosis have been met. If all the preconditions have been met, the CPU executes the diagnosis. That is, the CPU determines whether the element resistance is within a predetermined range. If it is below the range, the CPU determines that the sensor has high element temperature abnormality. If the element resistance is above the range, the CPU determines that the sensor has low element temperature abnormality.

5 Claims, 19 Drawing Sheets

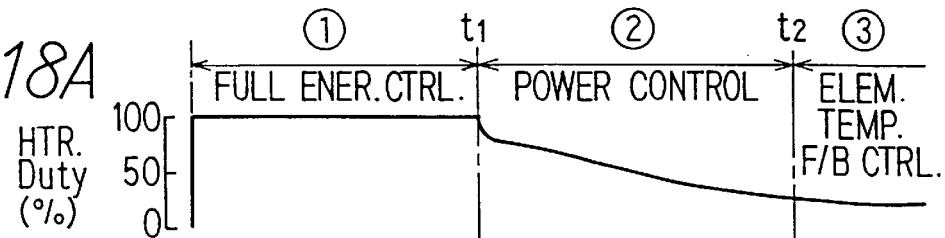
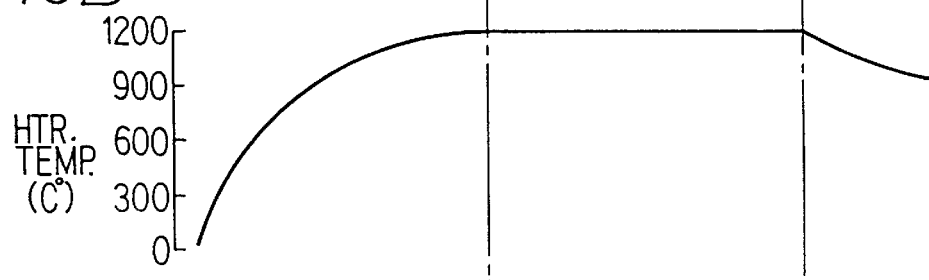
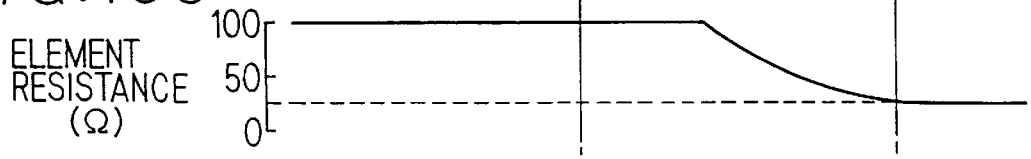

OXYGEN CONCENTRATION DETECTING APPARATUS

This application is a division of application Ser. No. 08/621,692, filed Mar. 26, 1996, which issued Jan. 20, 1998 as U.S. Pat. No. 5,709,198.

CROSS-REFERENCE TO RELATED APPLICATION

The present application is related to and claims priority from Japanese Patent Application No. Hei. 7-76338, incorporated herein by reference.

BACKGROUND OF THE INVENTION

1. Field of the Invention

The present invention relates to an oxygen concentration detecting apparatus having a limit current type oxygen sensor comprising an oxygen concentration detecting element that outputs limit current proportional to oxygen concentration and a heater for heating the detecting element and, more particularly, to an oxygen concentration detecting apparatus that checks for abnormality of the limit current type oxygen sensor.

2. Description of Related Art

Many modern air-fuel ratio control systems use limit current type oxygen sensors (oxygen concentration detectors). In such a system, the oxygen concentration detected by the air-fuel ratio sensor is inputted to a microcomputer to calculate an air-fuel ratio, and the microcomputer performs air-fuel ratio feedback control based on the calculated air-fuel ratio. The control system thereby achieves optimal combustion in the internal combustion engine and reduces harmful substances in exhaust gas, such as CO, HC, NOx and the like.

However, since the control precision of the air-fuel ratio control systems is heavily degraded if the reliability of detection of the air-fuel ratio deteriorates, there has been a strong demand for a technology that precisely detects an abnormality of an air-fuel ratio sensor. For example, Japanese Unexamined Patent Application Publication No. Hei. 1-232143, "Air-Fuel Ratio Control Apparatus for Internal Combustion Engine", describes a technology that detects an abnormality of a heater if the temperature of the air-fuel ratio sensor (oxygen concentration detecting element) detected by a temperature sensor fails to rise to a predetermined temperature. Japanese Unexamined Patent Application Publication No. Hei. 3-189350, "Oxygen Sensor Heater Control Apparatus", describes a technology for use in an apparatus for controlling the power supply to the heater so that the heater resistance becomes equal to a target resistance, the technology detecting an abnormality of the target resistance if the power supply to the heater deviates from a predetermined range.

However, the conventional art has the following problems. The aforementioned former technology (Japanese Unexamined Patent Application Publication No. Hei. 1-232143) requires a sensor for detecting the temperature of the air-fuel ratio sensor, and thus has problems of high costs. The latter technology (Japanese Unexamined Patent Application Publication No. Hei. 3-189350) merely determines whether the target resistance is properly set, and the occasions when this diagnosis technology detects abnormality are substantially limited to the occasions when the battery or the sensor has been replaced. Thus, this technology does not make a determination regarding the reliability of the oxygen sensor.

SUMMARY OF THE INVENTION

In view of the problems of the conventional art, an object of the present invention is to propose a novel diagnosis technology and thereby provide an oxygen concentration detecting apparatus that precisely and easily checks for abnormality of a limit current type oxygen sensor.

This object is achieved according to a first aspect of the present invention by providing an oxygen concentration detecting apparatus which determines whether the oxygen sensor is abnormal on the basis of whether the element temperature of the oxygen sensor is within a predetermined range. Thereby, this apparatus precisely and easily performs the sensor diagnosis.

Preferably, the oxygen concentration detecting apparatus performs the sensor diagnosis to distinguish a low element temperature abnormality and a high element temperature abnormality.

It is also possible that the oxygen concentration detecting apparatus determines whether the oxygen sensor is abnormal on the basis of whether the output from the oxygen sensor has changed within a predetermined range in response to an increase or a decrease of the fuel supply. Thus, this construction precisely and easily performs the sensor diagnosis.

Moreover, it is possible that the oxygen concentration detecting apparatus performs the sensor diagnosis when the oxygen sensor is or must be activated, thus achieving accurate diagnosis.

Further, the system may feedback-control the heater power supply to make the element temperature of the oxygen sensor substantially equal to a target element temperature and perform the diagnosis of the oxygen sensor on the basis of whether the heater power supply is greater than a predetermined abnormality determination criterion. Thus, this system precisely and easily performs the sensor diagnosis.

Also, the apparatus may achieve optimal diagnosis in accordance with the operating conditions of the engine.

The apparatus may perform the diagnosis of the oxygen sensor on the basis of whether the accumulation of the heater power supply is greater than a predetermined abnormality determination criterion. Thus, this apparatus enhances the precision of diagnosis data and achieves accurate diagnosis.

Moreover, the apparatus may allow the sensor diagnosis to be executed only if the initial heater resistance is equal to or less than a predetermined value that indicates the cold state of the oxygen sensor. Thus, the apparatus inhibits the sensor diagnosis, for example, when the engine is restarted after warming up and the accumulation of the heater power supply is relatively small, thereby maintaining the high precision of the sensor diagnosis.

Other objects and features of the invention will appear in the course of the description thereof, which follows.

BRIEF DESCRIPTION OF THE DRAWINGS

Additional objects and advantages of the present invention will be more readily apparent from the following detailed description of preferred embodiments thereof when taken together with the accompanying drawings in which:

FIGS. 18A–18E are timing charts indicating the operation of heater control according to a fifth embodiment;

FIGS. 19, 19A and 19B are a flowchart illustrating a heater control routine according to the fifth embodiment;

DETAILED DESCRIPTION OF THE PRESENTLY PREFERRED EXEMPLARY EMBODIMENTS

A first embodiment of the present invention wherein the oxygen concentration detecting apparatus of the present invention is embodied in an air-fuel ratio control apparatus of an automotive internal combustion engine will be described with reference to the accompanying drawings.

Figure 1:
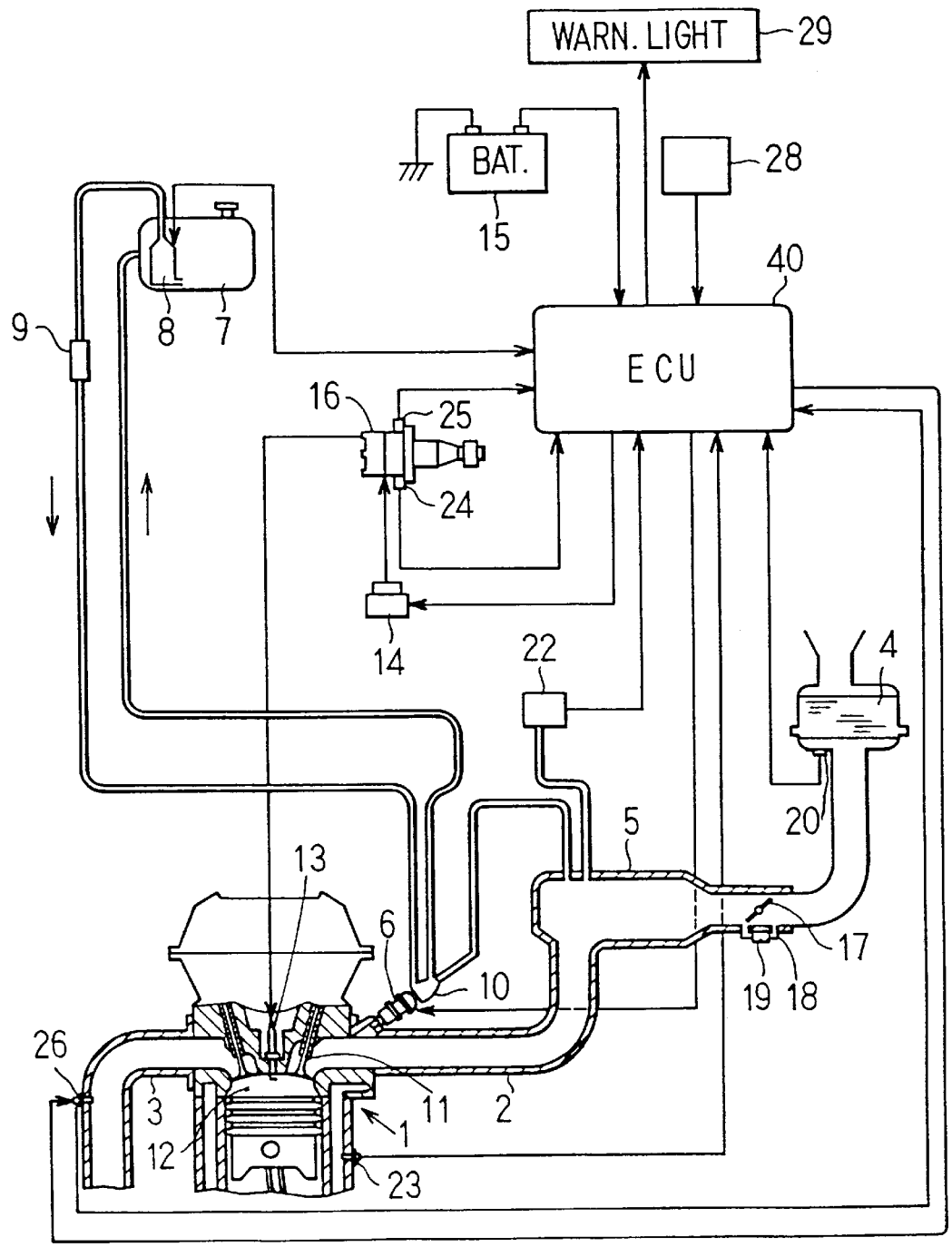
FIG. 1 schematically illustrates the overall construction of an air-fuel ratio control apparatus according to an embodiment of the invention.

FIG. 1 schematically illustrates the overall construction of the air-fuel ratio control apparatus of the internal combustion engine according to the first embodiment of the present invention. Referring to FIG. 1, a four-cylinder spark-ignition type gasoline internal combustion engine (hereinafter, referred to as "engine") 1 is connected to an intake pipe 2 and an exhaust pipe 3. An air cleaner 4 is provided in a most upstream portion of the intake pipe 2. A surge tank 5 is provided near the middle of the intake pipe 2. Disposed upstream from the surge tank 5 is a throttle valve 17 that is operated responsive to the depression of an accelerator pedal (not shown). A bypass passage 18 bypassing the throttle valve 1 is provided with an ISC valve (idle speed control valve) 19.

The intake pipe (intake ports) 2 connected to each cylinder of the engine 1 is provided with an injector 6 thereat. Fuel is pumped from a fuel tank 7 by a fuel pump 8, and then supplied to a pressure regulator 10 via a fuel filter 9. The pressure regulator 10 supplies the injector 6 with fuel with a regulated constant pressure, and also returns surplus fuel to the fuel tank 7. The injector 6 opens its valve to inject fuel by power supply from a battery 15. The fuel injected from the injector 6 is mixed with intake air to form a fuel-air mixture. The mixture is then introduced into a combustion chamber 12 by an intake valve 11.

An intake air temperature sensor 20 is disposed near the air cleaner 4 to detect the temperature of intake air. The surge tank 5 is provided with an intake pipe pressure sensor 22 for detecting the pressure inside the intake pipe 2 (intake negative pressure). The cylinder block of the engine 1 is provided with a coolant temperature sensor for detecting the temperature of the engine coolant.

A spark plug 13 is disposed in the combustion chamber 12 of each cylinder. An ignitor 14 generates a high voltage from the voltage supplied from the battery 15. The high voltage is then distributed to the spark plug 13 of each cylinder by a distributor 16. The distributor 16 comprises a cylinder distinguishing sensor 24 and a crank angle sensor 25. The crank angle sensor 25 generates crank angle signals at predetermined crank angles (for example, every 30° CA) during revolution of the crankshaft of the engine 1. The cylinder distinguishing sensor 24 generates cylinder distinguishing signals at a specific timing with respect to a specific cylinder (for example, the compression TDC of the first cylinder) during revolution of the crankshaft of the engine 1.

The exhaust pipe 3 of the engine 1 is provided with a limit current type oxygen sensor 26 that outputs detection signals linear with (proportional to) the oxygen concentration in exhaust gas. Disposed downstream from the oxygen sensor 26 is a catalytic converter that cleans exhaust gas.

The detection signals from the aforementioned sensors are inputted to an electronic control unit (hereinafter, referred to as "ECU") 40. The ECU 40 operates on the power supply from the battery 15. Upon receiving an ON-signal from an ignition switch 28, the ECU 40 starts the engine 1. During operation of the engine 1, the ECU 40 feedback-controls the air-fuel ratio approximately to a target air-fuel ratio (for example, the theoretically optimal air-fuel ratio) by varying the air-fuel ratio correction coefficient on the basis of the signals from the oxygen sensor 26. Furthermore, the ECU 40 performs sensor diagnosis operation (described later) to determine whether an abnormality has occurred in the oxygen sensor 26, and when an abnormality has occurred, turns on a warning light 29 to inform the driver of the abnormality.

Figure 2:
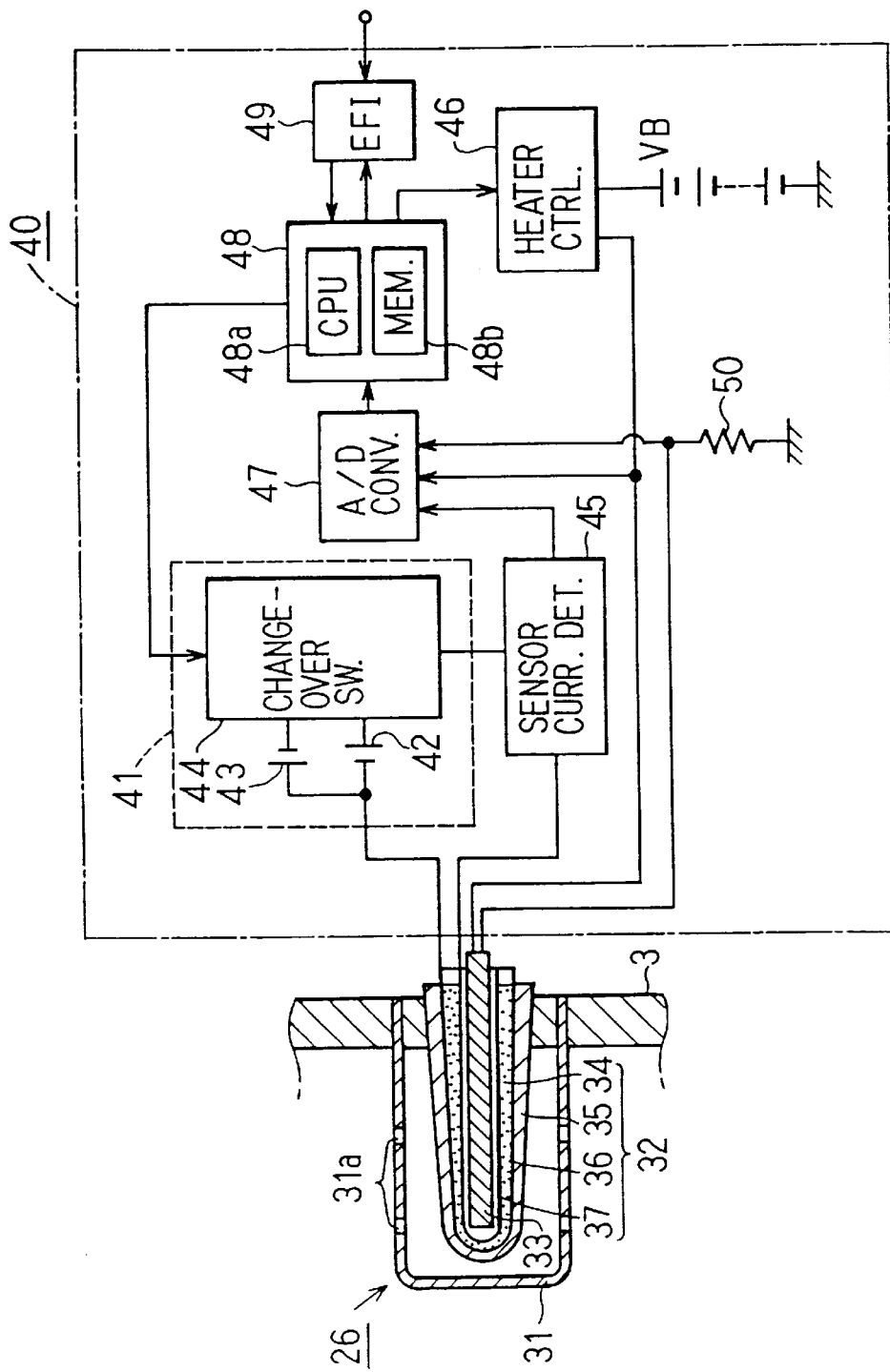
FIG. 2 illustrates a sectional view of an oxygen sensor and the circuit construction of an ECU in the first embodiment.

FIG. 2 shows a schematic sectional view of the oxygen sensor 26 and the circuit construction of the ECU 40 connected to the oxygen sensor 26. The oxygen sensor 26 projects into the exhaust pipe 3, as shown in FIG. 2, and comprises a cover 31, a sensor body 32 and a heater 33. The cover 31 has a generally "U" sectional shape, and its peripheral wall has many pores 31a that connect the interior of the cover 31 and its exterior. The sensor body 32 produces limit current corresponding to the oxygen concentration in the lean region of the air-fuel ratio or the concentration of carbon monoxide (CO) in the rich region of the air-fuel ratio.

The construction of the sensor body 32 will be described in detail. An exhaust gas-side electrode layer 36 is fixed onto the outer surface of a solid electrolyte layer 34 having a sectional shape of a cup. The inner surface of the solid electrolyte layer 34 is fixed to the atmosphere-side electrode layer 37. A diffused resistor layer 35 has been formed on the outside of the exhaust gas-side electrode layer 36 by plasma spraying. The solid electrolyte layer 34 is composed of an oxygen ion-conductive oxide sintered material in which a stabilizer, such as CaO, MgO, $Y_2O_3$ or $Yb_2O_3$ is dissolved in $ZrO_2$, $HfO_2$, $ThO_2$, $Bi_2O_3$ or the like. The diffused resistor layer 35 is composed of a heat-resistant inorganic substance such as alumina, magnesia, quartzite, spinel, or mullite. The exhaust gas-side electrode layer 36 and the atmosphere-side electrode layer 37 are composed of a precious metal having high catalytic activity, such as platinum, and are provided with a chemically plated porous coating. The exhaust gas-side electrode layer 36 has a surface area of about 10–100 $mm^2$ and a thickness of about 0.5–2.0 $\mu m$. The atmosphere-side electrode layer 37 has a surface area of 10 $mm^2$ or larger and a thickness of about 0.5–2.0 $\mu m$. The solid electrolyte layer 34 corresponds to the oxygen concentration detecting element in the appended claims.

The heater 33 is disposed in a space surrounded by the atmosphere-side electrode layer 37. The thermal energy from the heater 33 heats the sensor body 32 (the atmosphere-side electrode layer 37, the solid electrolyte layer 34, the exhaust gas-side electrode layer 36 and the diffused resistor layer 35). The heater 33 has a sufficient heat generating capacity to activate the sensor body 32.

With this construction of the oxygen sensor 26, the sensor body 32 generates a variable electromotive force at the point of the theoretical air-fuel ratio, and produces limit current in accordance with the oxygen concentration within the lean region defined with respect to the theoretical air-fuel ratio. The limit current in accordance with the oxygen concentration varies depending on the area of the exhaust gas-side electrode layer 36, the thickness of the diffused resistor layer 35, the porosity and the average pore size. The sensor body 32 linearly detects the oxygen concentration. However, since a high temperature of about 650° C. or higher is needed to activate the sensor body 32 and the activation temperature range of the sensor body 32 is relatively narrow, the thermal energy of exhaust gas from the engine 1 is not sufficient to control the activation of the sensor body 32. According to this embodiment, the heater 33 is controlled as described later to achieve control of the temperature of the sensor body 32. Within a rich region with respect to the theoretical air-fuel ratio, on the other hand, the concentration of carbon monoxide (CO), that is, an unburned gas, varies substantially linearly with the air-fuel ratio. The sensor body 32 generates limit current in accordance with the CO concentration in the rich region.

The voltage-current characteristics of the sensor body 32 will be described with reference to FIG. 3. The current-voltage characteristic curves in FIG. 3 indicate that the current flowing into the solid electrolyte layer 34 of the sensor body 32 in proportion to the oxygen concentration (air-fuel ratio) detected by the oxygen sensor 26 is linear with the voltage applied to the solid electrolyte layer 34. When the sensor body 32 is in the activated state at a temperature T=T1, the current-voltage characteristics of the sensor body 32 exhibit a stable state as indicated by characteristic curve L1 represented by solid lines in FIG. 3. The straight segments of the characteristic curve L1 parallel to the voltage axis V specify limit currents occurring in the sensor body 32. The variation of the limit current parallels the variation of the air-fuel ratio (that is, lean or rich). More precisely, the limit current increases as the air-fuel ratio shifts further to the lean side, and the limit current decreases as the air-fuel ratio shifts further to the rich side.

The region of the voltage-current characteristic curve where the voltage is smaller than the levels corresponding to the straight segments parallel to the voltage axis v is a resistance-dominant region. The slope of the characteristic curve L1 within such a resistance-dominant region is determined by the internal resistance of the solid electrolyte layer 34 provided in the sensor body 32 (hereinafter, referred to as "element resistance"). The element resistance varies with temperature. As the temperature of the sensor body 32 decreases, the element resistance increases and, therefore, the slope is reduced. When the temperature T of the sensor body 32 is T2 which is lower than T1, the current-voltage characteristics of the sensor body 32 become as indicated by the characteristic curve L2 represented by broken lines in FIG. 3. The straight segments of the characteristic curve L2 parallel to the voltage axis V specify limit currents occurring in the sensor body 32. The limit currents determined by the characteristic curve L2 are substantially equal to those determined by the curve L1.

Figure 3:
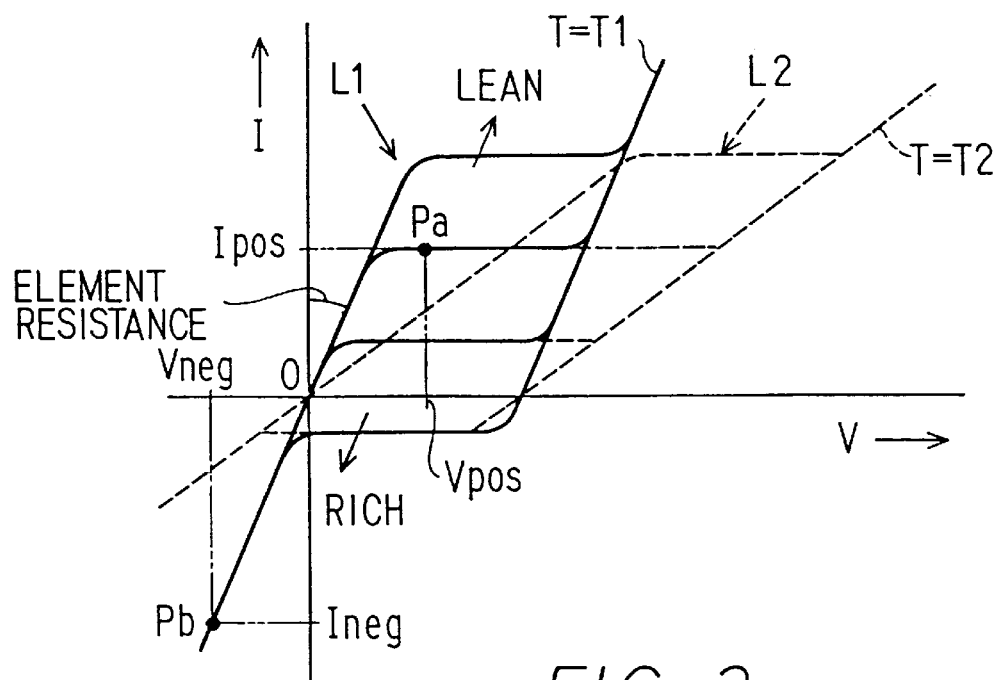
FIG. 3 is a graph indicating the voltage-current characteristics of the oxygen sensor according to the first embodiment.

With the characteristic curve L1, if a positive voltage is applied to the solid electrolyte layer 34 of the sensor body 32, the current flowing through the sensor body 32 becomes a limit current Ipos (see point Pa in FIG. 3). If a negative voltage is applied to the solid electrolyte layer 34 of the sensor body 32, the current through the sensor body 32 becomes a negative limit current Ineg that is not dependent on the oxygen concentration but is instead proportional solely to the temperature (see point Pb in FIG. 3).

Referring again to FIG. 2, the exhaust gas-side electrode layer 36 of the sensor body 32 is connected to a bias control circuit 41 that is connected to the atmosphere-side electrode layer 37 of the sensor body 32 via a positive bias DC power source 42. The bias control circuit 41 is generally composed of the positive bias DC power source 42, a negative bias DC power source 43 and a change-over switch circuit 44. The negative electrode of the positive bias DC power source 42 and the positive electrode of the negative bias DC power source 43 are connected to the exhaust gas-side electrode layer 36.

The change-over switch circuit 44 selectively connects only the positive electrode of the positive bias DC power source 42 to a sensor current detecting circuit 45 when switched to a first select state. When switched to a second select state, the change-over switch circuit 44 connects only the negative electrode of the negative bias DC power source 43 to the sensor current detecting circuit 45. That is, when the change-over switch circuit 44 is in the first select state, the positive bias DC power source 42 positively biases the solid electrolyte layer 34 of the sensor body 32 so that current flows through the solid electrolyte layer 34 in the positive direction. On the other hand, when the change-over switch circuit 44 is in the second select state, the negative bias DC power source 43 negatively biases the solid electrolyte layer 34 so that current flows through the solid electrolyte layer 34 in the negative direction. The terminal voltages of the positive and negative bias DC power sources 42, 43 correspond to the aforementioned applied voltages Ipos, Ineg, respectively.

The sensor detecting circuit 45 detects the current flowing from the atmosphere-side electrode layer 37 of the sensor body 32 to the switch circuit 44 or in the reverse direction, that is, the current flowing through the solid electrolyte layer 34. A heater control circuit 46 duty-cycle controls the power supplied from a battery power source VB to the heater 33 in accordance with the heater temperature and/or the element temperature of the oxygen sensor 26, thus controlling the heating by the heater 33. The current flowing through the heater 33 (hereinafter, referred to as "heater current Ih") is detected by a current detecting resistor 50.

An A/D converter 47 converts the current detected by the sensor current detecting circuit 45 (Ipos, Ineg indicated in FIG. 3), the heater current Ih, and the voltage applied to the heater 33 (hereinafter, referred to as "heater voltage Vh") into digital signals, and outputs the signals to a microprocessor 48. The microprocessor 48 comprises a CPU 48a for executing various operations and a memory 48b composed of a ROM and a RAM. In accordance with predetermined computer programs, the microprocessor 48 controls the bias control circuit 41, the heater control circuit 46 and a fuel injection control apparatus (hereinafter, referred to as "EFI") 49. The EFI 49 receives various signals from the aforementioned sensors as engine information and thereby detects intake air temperature Tam, intake negative pressure Pm, coolant temperature Thw, engine speed, NE, vehicle speed Vs and the like. Based on such engine information, the EFI 49 controls the fuel injection performed by the injector 6. According to this embodiment, the CPU 48a of the microcomputer 48 constitutes heater control means, element resistance detecting means, sensor diagnostic means, and heater power supply estimating means as recited in the appended claims.

The operation of this embodiment will be described with reference to the control programs executed by of the CPU 48a of the microcomputer 48. Described hereinafter are heater energization control, air-fuel ratio detecting operation, and then sensor diagnosis operation.

Figure 4:
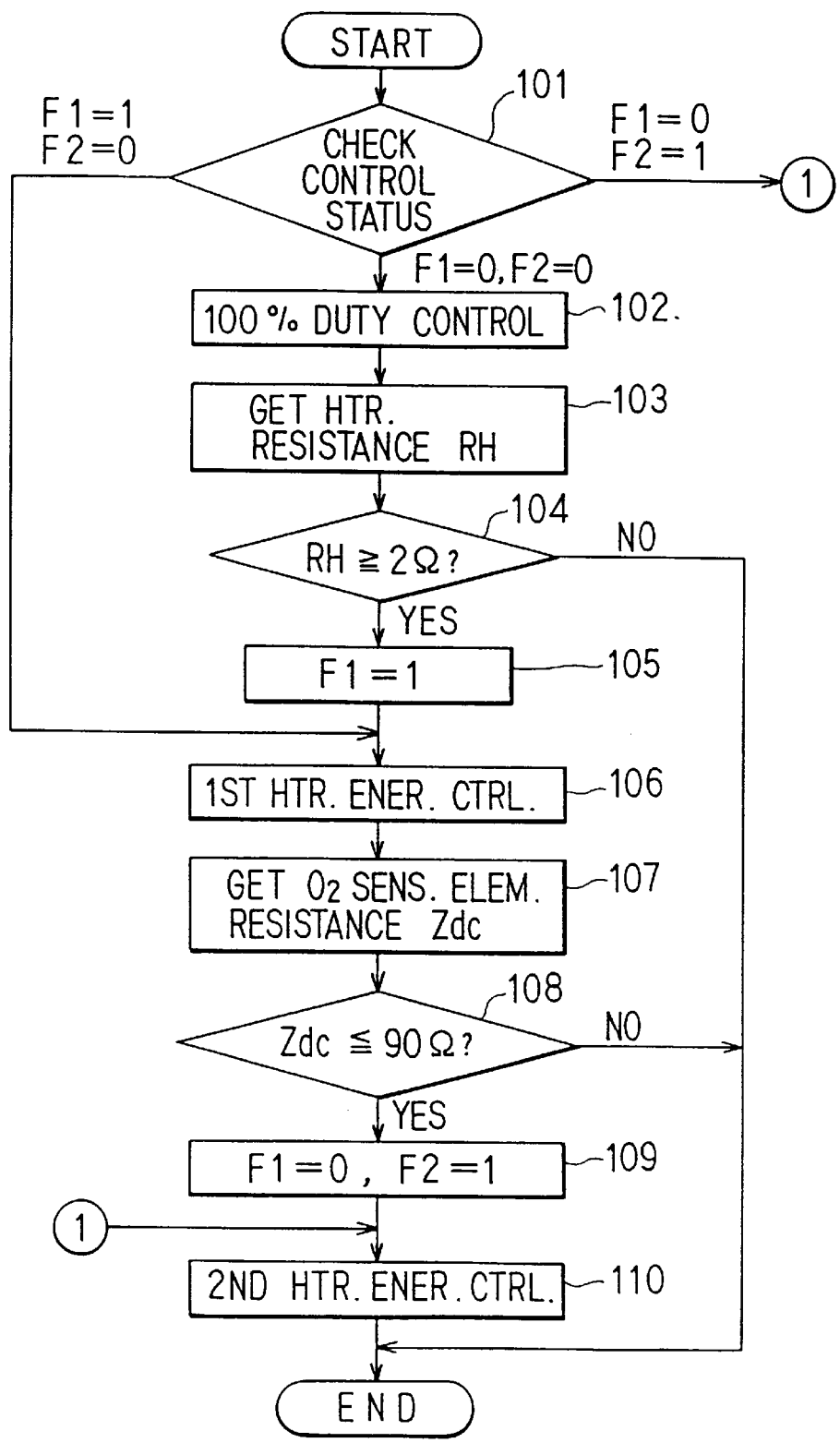
FIG. 4 is a flowchart illustrating a heater energization control routine of the first embodiment.

The flowchart of FIG. 4 illustrates a heater energization control routine executed in a predetermined cycle by the CPU 48a. In step 101, the CPU 48a determines the control state of the heater 33 on the basis of heater control flags F1, F2. According to the first embodiment, following the turning-on of the ignition switch 28, the heater control mode shifts to 100% duty control, first heater energization control, and then second heater energization control in that order. The heater control flag F1=1 indicates that the first heater energization control is being performed. The heater control flag F2=1 indicates that the second heater energization control is being performed.

In an initial period of the heater energization control, the heater control flags F1, F2 have been cleared to "0" (initial value), and therefore the CPU 48a proceeds to step 102 to execute the 100% duty control. More specifically, the CPU 48a controls the heater control circuit 46 shown in FIG. 2 with 100% duty to fix the power supply to the heater 33 to the maximum value, thus rapidly heating the heater 33. In step 103, the CPU 48a reads in the heater resistance RH calculated on the basis of the heater voltage Vh and the heater current Ih (RH=Vh/Ih). The CPU 48a then determines in step 104 whether the heater resistance RH equals or exceeds 2 Ω (whether RH>2 Ω). If RH<2 Ω, then the CPU 48a immediately ends this routine. In this case, the 100% duty control is continued.

On the other hand, if step 104 determines that the heater resistance RH≧2 Ω, the CPU 48a proceeds to step 105 to set the heater control flag F1 to "1", and then proceeds to step 106 to execute the first heater energization control. In the first heater energization control, the control duty for the heater 33 is determined by using a first map based on the engine load (for example, the intake negative pressure Pm) and the engine speed NE. The first map has been arranged such that the element temperature of the oxygen sensor 26 will become a predetermined activating temperature; for example, a large control duty is set for a low-load or low-speed operational region since the thermal energy of exhaust gas is small in such a region. Once the flag F1 has been thus set, the CPU 48a jumps from step 101 to step 106 to execute the first heater energization control.

Figure 5:
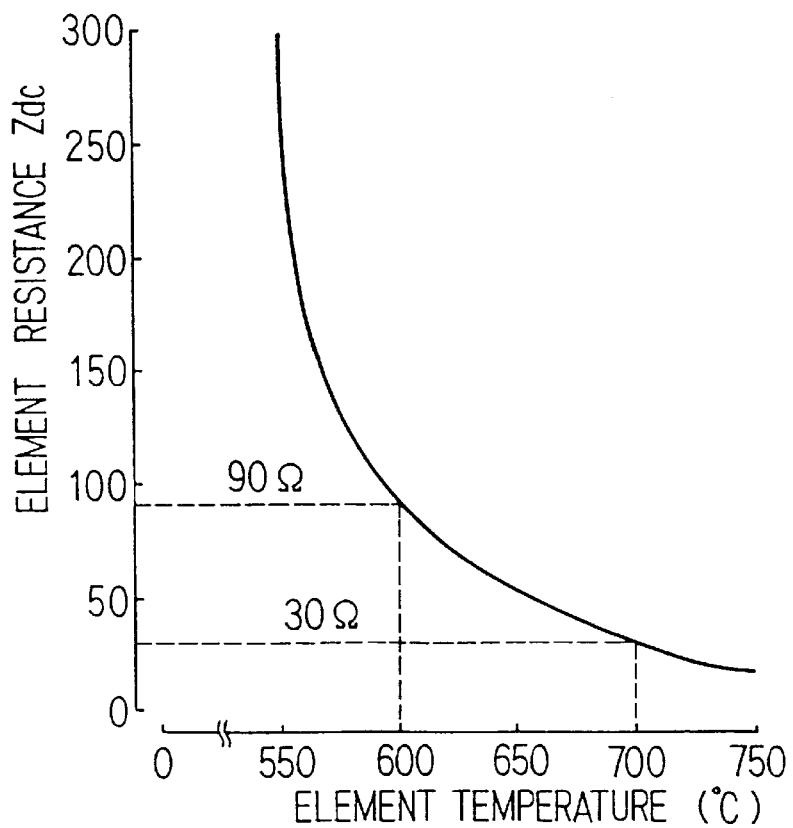
FIG. 5 is a graph indicating the relationship between the element temperature and the element resistance in the first embodiment.

In step 107 following step 106, the CPU 48a reads in the element resistance of the oxygen sensor 26 (the internal resistance of the solid electrolyte layer 34) Zdc. The element resistance Zdc is calculated on the basis of the element applied voltage Vneg (negative applied voltage) and the negative current. Ineg detected by the sensor current detecting circuit 45 (Zdc=Vneg/Ineg). In step 108, the CPU 48a determines whether the element resistance Zdc has become 90 Ω or lower (whether Zdc≦90 Ω). If Zdc>90 Ω, then the CPU 48a immediately ends the routine. In this case, the first heater energization control is continued. For reference, the relationship between the element temperature and the element resistance Zdc is indicated in FIG. 5.

On the other hand, if step 108 determines that Zdc≧90 Ω, then the CPU 48a proceeds to step 109 to set the flag F1 to "0" and the flag F2 to "1", and in step 110 executes the second heater energization control. The second heater energization control uses a second map, different from the first map, to determine a control duty for the heater 33 (of generally the same characteristics as in the first heater energization control) in accordance with the engine load (for example, the intake negative pressure Pm) and the engine speed NE. Once the flag F2=1 has been set, the CPU 48a jumps from step 101 to step 110 to execute the second heater energization control. As described above, this embodiment open-loop controls the energization of the heater 33 by the 100% duty control in the initial period of the control operation, and then by the first energization control followed by the second heater energization control.

Figure 6:
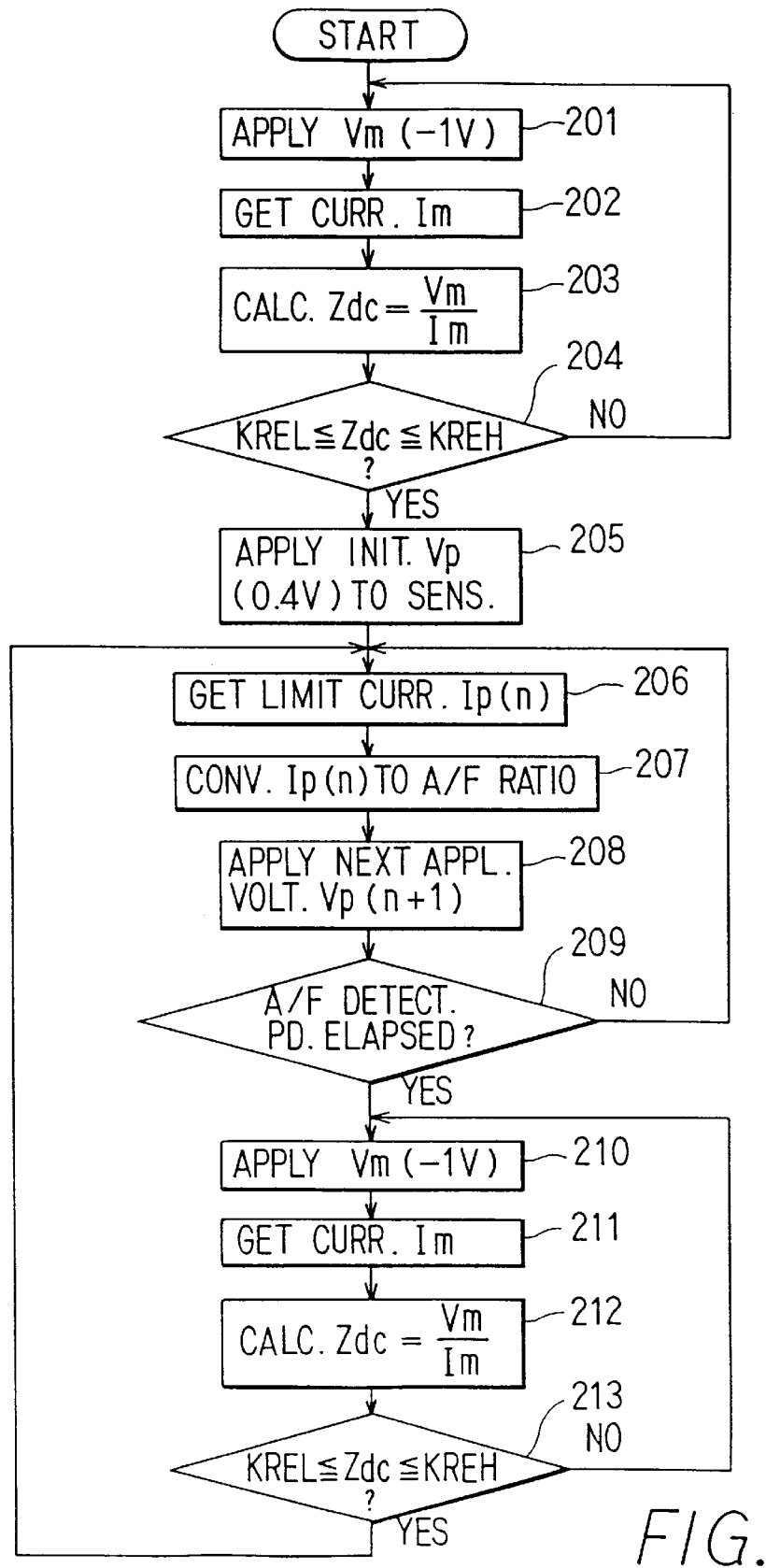
FIG. 6 is a flowchart illustrating an air-fuel ratio detecting routine of the first embodiment.

The flowchart of FIG. 6 illustrates an air-fuel ratio detecting routine started in response to the turning-on of the ignition switch 28 and executed by the CPU 48a in a cycle of, for example, 8 msec.

In steps 201–204 in FIG. 6, the CPU 48a executes procedures for determining activation of the sensor. Step 201 applies a predetermined voltage Vm within an element resistance detecting region indicated in FIG. 7 (for example, Vm=–1 volt). Step 202 reads in the current Im (see FIG. 7) detected by the sensor current detecting circuit 45 shown in FIG. 2. Step 203 calculates an element resistance Zdc based on the applied voltage Vm and the detected current Im (Zdc=Vm/Im).

In step 204, the CPU 48a determines whether the oxygen sensor 26 has been activated on the basis of whether the element resistance Zdc is within a predetermined activation range (KREL-KREH). More specifically, if KREL≦Zdc≦KREH, that is, step 204 makes an affirmative determination, then it is determined that the oxygen sensor 26 has been activated. The CPU 48a then proceeds to step 205. On the other hand, if step 204 makes negative determination, the CPU 48a repeats steps 201–204 until the sensor activation is determined.

Figure 7:
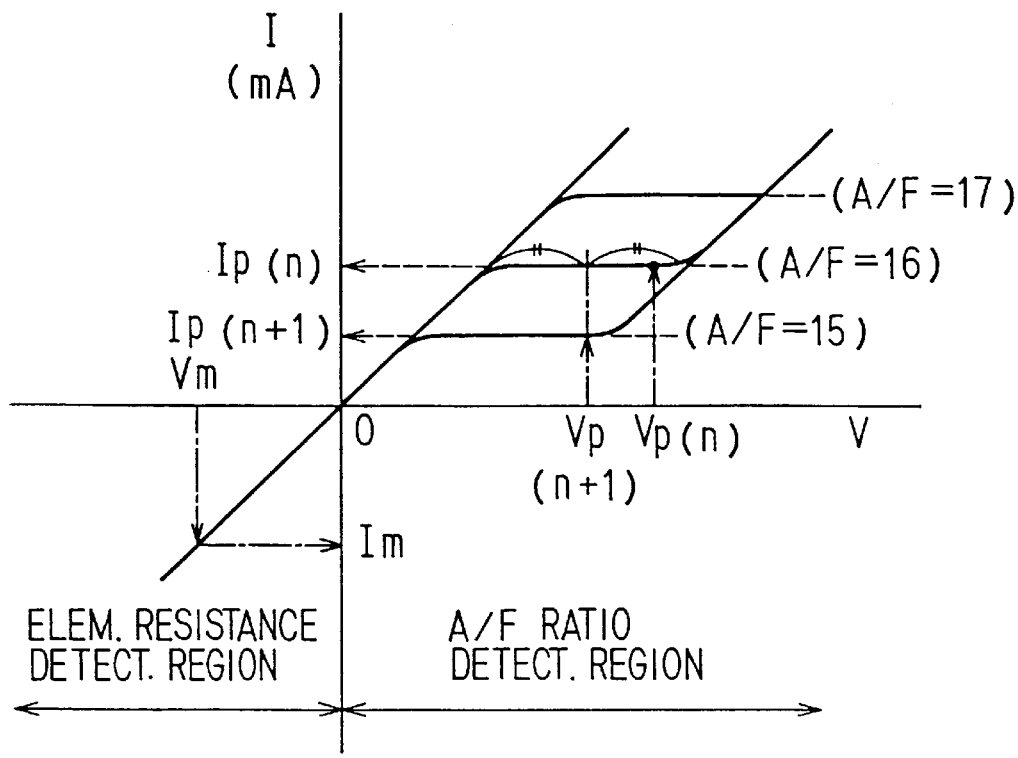
FIG. 7 is a graph indicating the current-voltage characteristics of the oxygen sensor of the first embodiment.

In step 205, the CPU 48a applies 0.4 volt to the oxygen sensor 26 as the initial value of the applied voltage Vp within an air-fuel ratio detecting range indicated in FIG. 7. Then in step 206, the CPU 48a reads in the limit current Ip(n) detected by the sensor current detecting circuit 45 shown in FIG. 2. The CPU 48a converts the limit current Ip(n) into an air-fuel ratio (A/F) in step 207. In step 208, the CPU 48a calculates an apply voltage Vp(n+1) for the next performance of the air-fuel ratio detection {Vp(+1)=f(Ip)}, and applies the apply voltage Vp (n+1) to the oxygen sensor 26. Referring to FIG. 7, if the air-fuel ratio is "16" in operation cycle (n) and "15" in operation cycle (n+1), application of Vp(n) results in detection of Ip(n) and then application of Vp(n+1) results in detection of Ip(n+1).

Then, CPU 48a determines in step 209 whether a predetermined length of time has elapsed following the start of the air-fuel ratio detection. If the predetermined length of time has not elapsed, the CPU 48a repeats steps 206–209. If the predetermined length of time has elapsed, the CPU 48a proceeds to step 210. In steps 210–213, the CPU 48a performs sensor activation determining operation as in steps 201–204.

More specifically, the CPU 48a determines in step 213 whether the element resistance Zdc determined through steps 210–212 is within the predetermined activation range (KREL-KREH). If KREL≦Zdc≦KREH, then it is determined that the oxygen sensor 26 has been activated. The CPU 48a then proceeds to step 206. On the other hand, if step 213 makes negative determination, the CPU 48a repeats steps 210–213.

Figure 8:
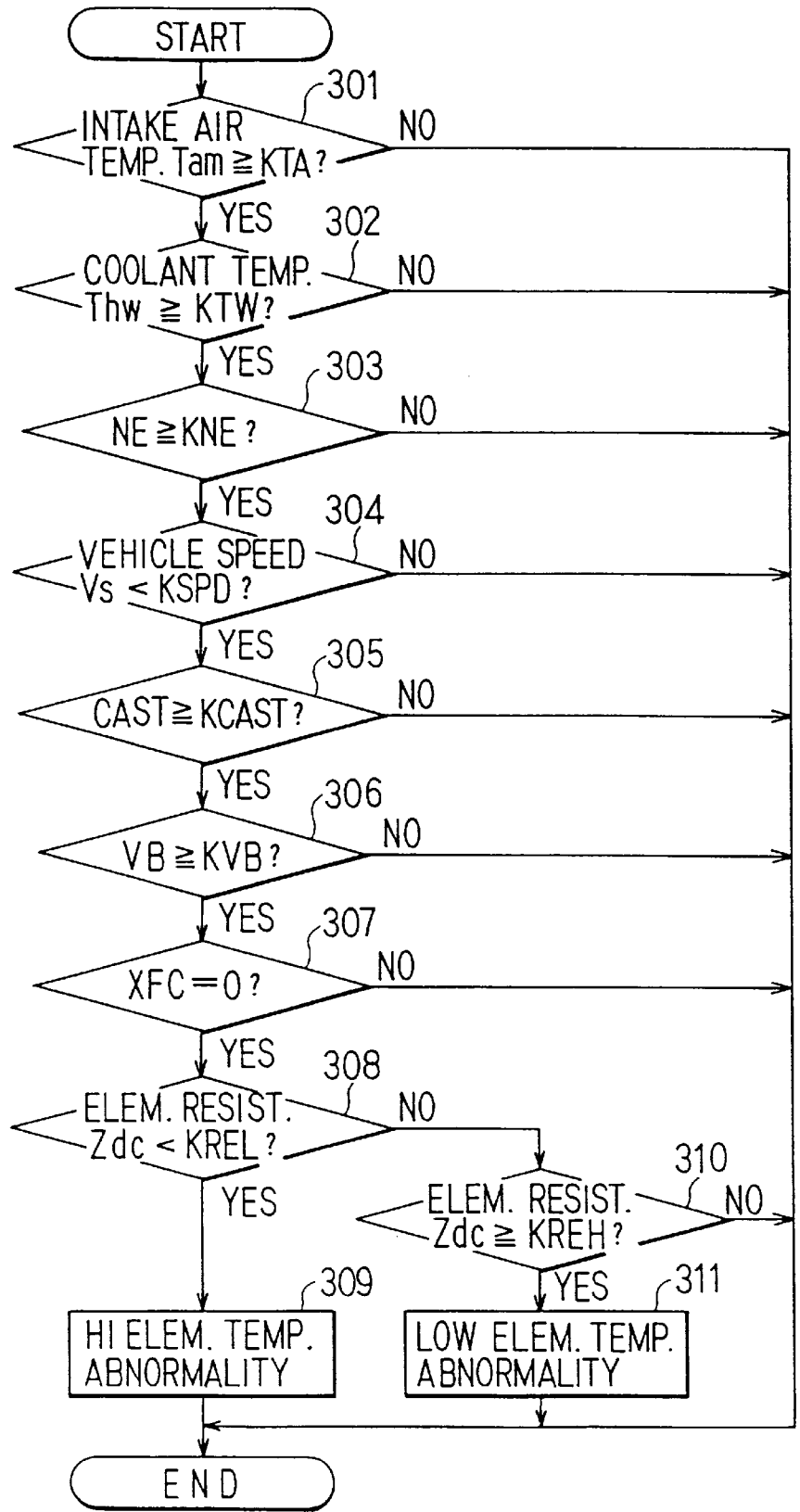
FIG. 8 is a flowchart illustrating a sensor diagnosis routine of the first embodiment.

The sensor diagnosis routine will be described with reference to FIG. 8. The routine as illustrated by the flowchart of FIG. 8 is executed by the CPU 48a in a predetermined cycle of, for example, 32 msec. Through steps 301–307 in FIG. 8, the CPU 48a determines whether preconditions for the sensor diagnosis have been established. More specifically, step 301 determined, whether the intake air temperature Tam equals or exceeds a predetermined criterion KTA (for example, 5° C.). Step 302 determines whether the coolant temperature Thw equals or exceeds a predetermined criterion KTW (for example, 5° C.). Step 303 determines whether the engine speed NE equals or exceeds a predetermined criterion KNE (for example, 500 rpm). Step 304 determines whether the vehicle speed Vs is less than a predetermined criterion KSPD (for example, 100 km/h). Step 305 determines whether the elapsed time CAST following the start of the engine 1 equals or exceeds a predetermined criterion KCAST (for example, 20 seconds). Step 305 determines whether the battery voltage VB equals or exceeds a predetermined criterion KVB (for example, 13 V). Step 307 determines whether a fuel cut flag XFC for indication of performance of fuel-cut operation is cleared to "0", that is, whether the fuel cut operation remains unperformed.

Of the aforementioned preconditions, the elapsed time CAST following the start of the engine 1 and the battery voltage VB are used to estimate an accumulated heater power supply. It is determined that the accumulation of heater power supply has reached or exceeded a predetermined value when these values become equal to or greater than predetermined values. If these conditions have been established, it is assumed that the oxygen sensor 26 has been activated or must be activated, and the CPU 48a allows the diagnosis to be performed. These preconditions for diagnosis provide precise diagnosis.

If any of steps 301–307 makes a negative determination, the CPU 48a immediately ends this routine. If all of steps 301–307 make affirmative determinations, the CPU 48a proceeds to step 308 to execute the sensor diagnosis based on the element resistance Zdc of the oxygen sensor 26. The element resistance Zdc of the oxygen sensor 26 is calculated as in steps 201–203 described above.

In step 308, the CPU 48a determines whether the element resistance Zdc is less than a first criterion KREL (10 Ω according to this embodiment). If Zdc<KREL, the CPU 48a proceeds to step 309. The element resistance Zdc less than the first criterion KREL means that the element temperature has risen too high. In this case, the CPU 48a determines that the oxygen sensor 26 has a "high element temperature abnormality". The high element temperature abnormality includes the following modes: a mode wherein the heater resistance of the oxygen sensor 26 varies to smaller values to allow excessively large currents; and a mode wherein the ground-side wire harness of the heater 33 is constantly short-circuited to ground so that the current control fails, thus allowing excessively large currents.

On the other hand, if Zdc≧KREL, the CPU 48a determines in step 310 whether the element resistance Zdc equals or exceeds the second criterion KREH (90 Ω according to this embodiment). If Zdc≧KREH, then the CPU 48a proceeds to step 311. The element resistance Zdc equaling or exceeding the second criterion KREH means that the element temperature has remained too low. Therefore, the CPU 48a determines in step 311 that the oxygen sensor 26 has a "low element temperature abnormality". The low element temperature abnormality includes the following modes: a mode wherein the heater resistance of the oxygen sensor 26 varies to large values, thereby reducing the current; a mode wherein the heater 33 deteriorates to increase its resistance, thereby reducing the current; and a mode wherein the wire harness of the heater 33 is disconnected, thus preventing the current from passing through the sensor.

Figure 9:
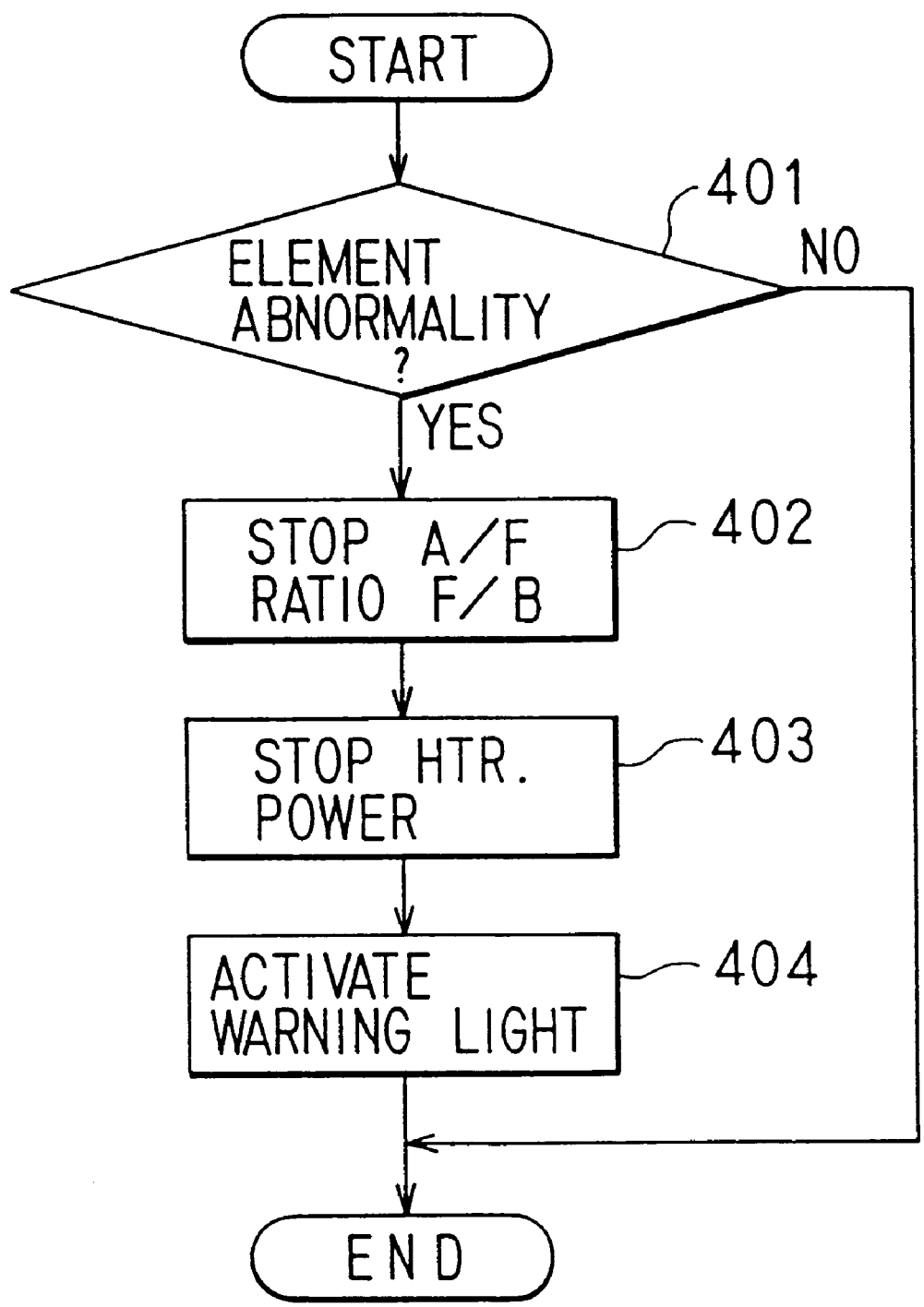
FIG. 9 is a flowchart illustrating a fail-safe routine of the first embodiment.

If the aforementioned element abnormality of oxygen sensor 26 is determined, a fail-safe routine illustrated in FIG. 9 is performed (for example, in a cycle of 32 msec). In step 401 in FIG. 9, the CPU 48a determines whether the element abnormality has occurred. If the element abnormality (high temperature abnormality or lower temperature abnormality) has been determined in the operation illustrated in FIG. 8, the CPU 48a proceeds to step 402 to stop the air-fuel ratio feedback. Then, the CPU 48a discontinues the energization of the heater 33 in step 403, and turns on the warning light 29 to indicate occurrence of the element abnormality in step 404. The procedure of step 404 may be designed to indicate the high temperature abnormality and the low temperature abnormality in separate manners.

As described above, the first embodiment determines whether abnormality has occurred in the oxygen sensor 26 on the basis of whether the element resistance of the oxygen sensor 26 is within the predetermined range (steps 308–311 in FIG. 8). More specifically, the output characteristics of the limit current type oxygen sensor 26 are determined or specified by the slope of the characteristic curve within the resistance-dominant region as shown in FIG. 3 (the slope of a segment of the curve corresponding to voltages smaller than the voltages corresponding to the straight segment of the curve parallel to the voltage axis), that is, the magnitude of the element resistance. If the oxygen sensor 26 is abnormal, the element resistance becomes too large or too small. Utilizing this phenomenon, abnormality of the oxygen sensor 26 can be precisely and easily determined.

In addition, this embodiment determines whether the oxygen sensor 26 has low element temperature abnormality (or high element temperature abnormality) on the basis of whether the element resistance of the oxygen sensor 26 is above (or below) the allowed range. More specifically, if the element resistance is too high, it can be reasonably considered that the element temperature is too low, and thus the low element temperature abnormality is determined. If the element resistance is too low, it can be reasonably considered that the element temperature is too high, and thus the high element temperature abnormality is determined.

Furthermore, since unlike the conventional art, this embodiment requires no temperature sensor for detecting the element temperature, the embodiment will not suffer from a cost increase. Although a conventional device can determine abnormality of the oxygen sensor mainly when the battery or the sensor has been replaced, this embodiment constantly checks for abnormality of the sensor during the traveling of the vehicle. Thus, this embodiment improves the reliability of the output from the sensor and can provide a high-precision air-fuel ratio control system.

Although the first embodiment performs the 100% duty control, the first heater energization control and the second heater energization control in that order, the method of heater energization control is not limited by this embodiment. The other methods that may be employed are, for example: a method in which only the first and second heater energization controls are performed; and a method in which the 100% duty control is performed for a predetermined length of time following the start of the engine, and then, for later operation, only the first and second heater energization controls are performed.

Second Embodiment

Figure 10:
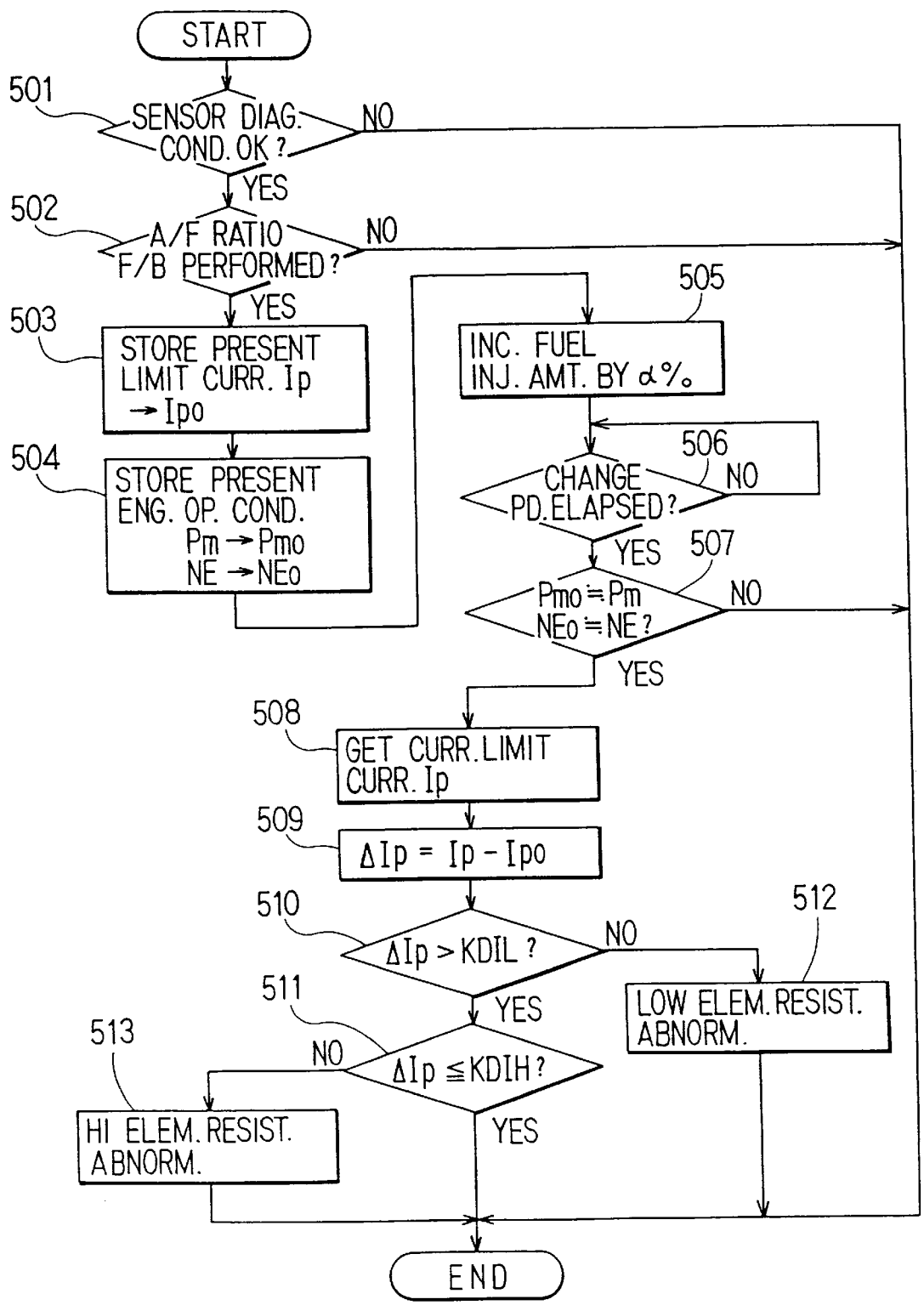
FIG. 10 is a flowchart illustrating sensor diagnosis routine according to a second embodiment of the present invention.

A second embodiment will be described mainly by referring to the features distinguishing this embodiment from the first embodiment. According to the second embodiment, the CPU 48a provided in the microprocessor 48 constitutes the heater control means, the fuel amount varying means and the sensor diagnostic means in the appended claims. FIG. 10 shows a sensor diagnosis routine according to the second embodiment.

In step 501 in FIG. 10, the CPU 48a determines whether preconditions for the sensor diagnosis have been established. The determination regarding the preconditions in step 501 corresponds to steps 301–307 in FIG. 8. In step 502, the CPU 48a determines whether the air-fuel ratio feedback is being performed. If either step 501 or step 502 makes a negative determination, the CPU 48a ends this routine. If both step 501 and step 502 make an affirmative determination, the CPU 48a proceeds to step 503.

In step 503, the CPU 48a stores the limit current Ip presently detected by the sensor current detecting circuit shown in FIG. 2 as "Ipo". In step 504, the CPU 48a stores the present engine operating conditions (the intake negative pressure Pm, the engine speed NE) as "Pmo" and "NEo".

Then, the CPU 48a increases or decreases the amount of fuel to be injected by the injector 6 by α % (for example, 10%) in step 505, and then determines in step 506 whether a predetermined length of time has elapsed following the fuel increase or decrease. The fuel increase means that the air-fuel ratio is forcibly shifted to the rich side, and the fuel decrease means that the air-fuel ratio is forcibly shifted to the lean side. When the predetermined length of time has elapsed following the fuel increase or decrease, the CPU 48a proceeds to step 507 to determine whether the current intake negative pressure Pm and the current engine speed NE substantially equal the values "Pmo" and "NEo" detected before the fuel increase (the values stored in step 504). If step 507 determines that the engine operating conditions have changed, the CPU 48a immediately ends the routine without executing the sensor diagnosis. On the other hand, if step 507 determines that the engine operating conditions have not changed, the CPU 48a proceeds to step 508 to execute the sensor diagnosis.

In step 508, the CPU 48a reads in the limit current Ip presently detected by the sensor current detecting circuit 45. Then, step 509 calculates a current change ΔIp between the current values before and after the fuel increase (ΔIp=Ip−Ipo). The CPU 48a determines in step 510 whether the current change ΔIp (absolute value) is greater than a first current criterion KDIL (whether ΔIp>KDIL). Step 511 determines whether the current change ΔIp (absolute value) is equal to or less than a second current criterion KDIH (whether ΔIp≦KDIH, where KDIL<KDIH). The allowed range for current change (KDIL–KDIH) has been set corresponding to the actual change of the air-fuel ratio caused by the fuel increase.

If the current change ΔIp is within the range of KDIL–KDIH, CPU 48a makes affirmative determination in both step 510 and step 511. If ΔIp≦KDIL, CPU 48a makes negative determination in step 510 and then determines in step 512 that the low element temperature abnormality has occurred. If ΔIp>KDIH, the CPU 48a makes negative determination in step 511 and then determines in step 513 that the high element temperature abnormality has occurred.

Figure 11C:
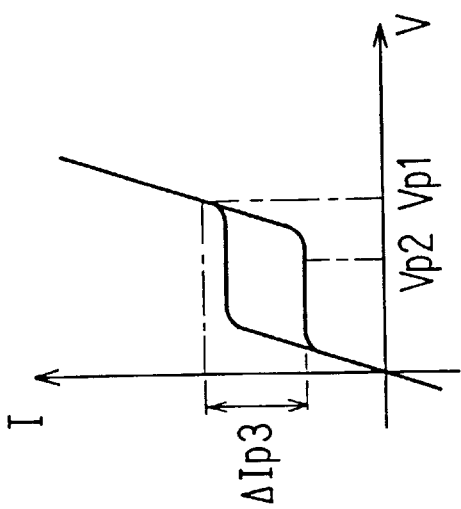
FIGS. 11A–11C are graphs indicating the current-voltage characteristics of the oxygen sensor, when the element is normal (FIG. 11A), when the element temperature is abnormally low (FIG. 11B), and when the element temperature is abnormally high (FIG. 11C), respectively.
Figure 11B:
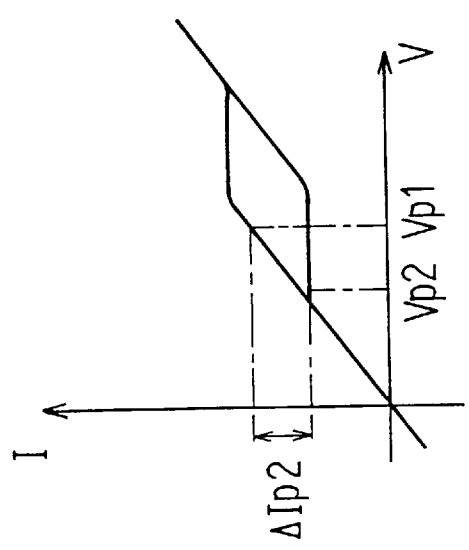
Figure 11A:
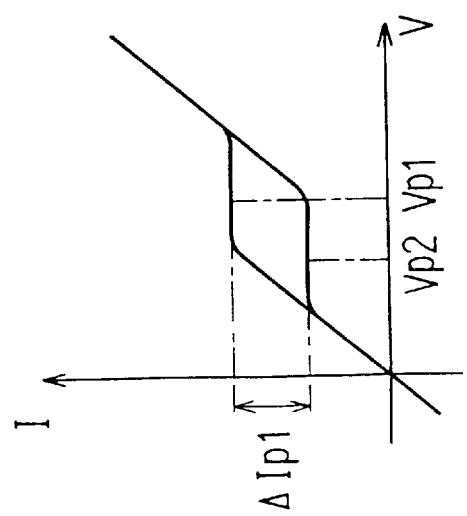
Figure 12A:
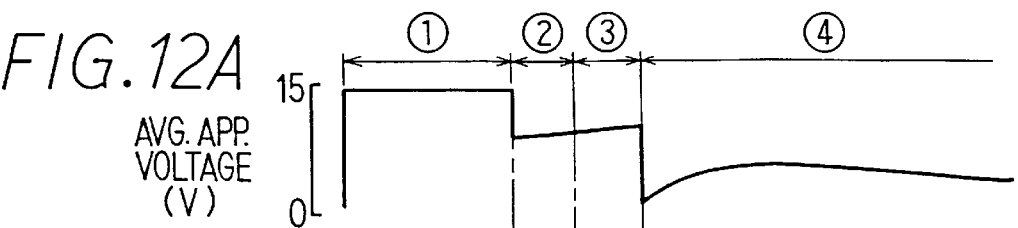
FIGS. 12A–12D are timing charts indicating the operation of heater control according to a third embodiment of the present invention.
Figure 12B:
Figure 12C:
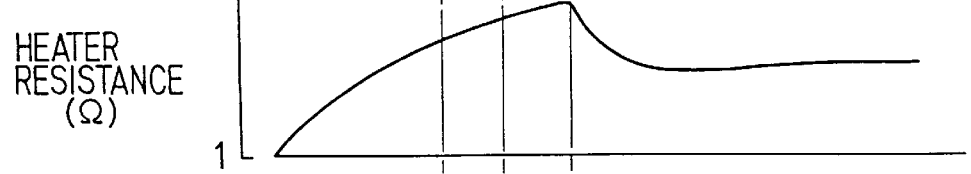
Figure 12D:
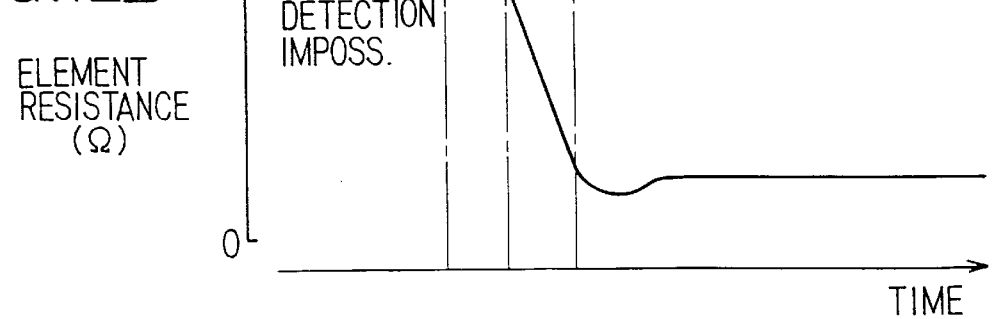

FIGS. 11A, 11B and 11C are graphs indicating the signals outputted from the oxygen sensor 26 when the oxygen it sensor 26 is normal, and when the oxygen sensor 26 has the low element temperature abnormality, and when the oxygen sensor 26 has the high element temperature abnormality, respectively. In the graphs, the current changes ΔIp1, ΔIp2, ΔIp3 represent changes of the limit current caused by the changing of the applied voltage from "Vp1" to "Vp2". If the oxygen sensor 26 has the low element temperature abnormality, the element resistance becomes large and the slope of the characteristic curve in the resistance-dominant region becomes small, as indicated in FIG. 11B. Thus, "ΔIp2" becomes smaller than "ΔIp1" that occurs in the normal conditions (ΔIp2<ΔIp1). In this case, step 510 in FIG. 10 makes a negative determination, and thus the low element temperature abnormality is determined. On the other hand, if the oxygen sensor 26 has the high element temperature abnormality, the element resistance becomes small and the slope of the curve in the resistance-dominant region becomes great, as indicated in FIG. 11C. Thus, "ΔIp3" becomes larger than "ΔIp1" that occurs in the normal conditions (ΔIp3>ΔIp1). In this case, step 511 in FIG. 10 makes a negative determination, and thus the high element temperature abnormality is determined.

As described above, the second embodiment increases the fuel supply to the engine 1 (in step 505 in FIG. 10), and determines whether the fuel increase has caused a change of the output (limit current) from the sensor 26 within the predetermined range in order to determine whether the oxygen sensor 26 has an abnormality (steps 510–513 in FIG. 10). With this procedure, it can be determined whether the shift of the air-fuel ratio to the rich side (decrease of the oxygen concentration) caused by the fuel increase is properly reflected in the sensor output, so that abnormality of the oxygen sensor 26 can be precisely and easily determined. In addition, since a criterion range is used for determination of abnormality, the embodiment is able to separately determine the low element temperature abnormality and the high element temperature abnormality.

Third Embodiment

A third embodiment will be described. While the first and second embodiments open-loop control the heater 33 of the oxygen sensor 26, the third embodiment controls the heater 33 with feedback of the element temperature. According to this embodiment, the CPU 48a provided in the microprocessor 48 constitutes the element resistance detecting means, the heater power supply control means and the sensor diagnostic means in the appended claims.

FIGS. 12A–12D show timing charts indicating heater control according to the third embodiment. More precisely, the timing charts indicate the operation of the heater control performed from the starting of energization of the heater 33 in response to the starting of the engine 1 until sufficient activation of the oxygen sensor 26. According to this embodiment, the heater control can be divided into four modes (1)–(4) as indicated in FIGS. 12A–12D, in view of the different purposes and control methods. These control modes will be described in sequence. The control modes (1)–(3) are performed to control the heater 33 before the oxygen sensor 26 is activated, and the control mode (4) is performed to control the heater 33 after the oxygen sensor 26 has been activated.

In the control mode (1) performed immediately after the starting of the engine 1, the 100% duty heater voltage is applied to the heater 33 (hereinafter, this control will be referred to as "full energization control"). That is, the maximum voltage is supplied to the heater 33 to quickly heat the heater 33 when the heater 33 and the sensor element (the sensor body 32) are cold.

The control modes (2) and (3) control the power supply to the heater 33 to maintain the heater temperature at a target heater temperature (for example, 1200° C.; that is, the upper limit heater temperature). Hereinafter, these control modes will be referred to as "power control". Since the heater temperature is specifically determined by the power supply to the heater 33 if the element temperature is substantially the activation temperature (700° C.), the temperature of the heater 33 can be maintained at a constant level in such a case by continuing to supply a predetermined power. However, if the element temperature is low, the power supply needed to maintain the heater temperature at a constant level varies with the element temperature. Normally, as the element temperature is lower, the power supply required is larger. During the power control, the power supply to the heater 33 is controlled in accordance with the element resistance (having the relationship with the element temperature as indicated in FIG. 5).

However, in an initial period of the power control, the element resistance is considerably large; that is, it exceeds the maximum detectable value (for example, 600 Ω). In such an element resistance undetectable region, the power supply to the hater 33 is maintained at a constant level (for example, 60 W) (control mode (2)). When the element temperature is increased so that the element resistance becomes 600 Ω or lower, the power in accordance with the element resistance is then supplied to the heater 33 (control mode (3)).

The control mode (4) feedback-controls the power supply to the heater 33 to achieve an element resistance of 30 Ω (corresponding to an element temperature of 700° C.) in order to maintain the activation of the sensor element (hereinafter, referred to as "element temperature feedback control").

A heater control routine according to the third embodiment will be described with reference to FIG. 13.

Figure 13:
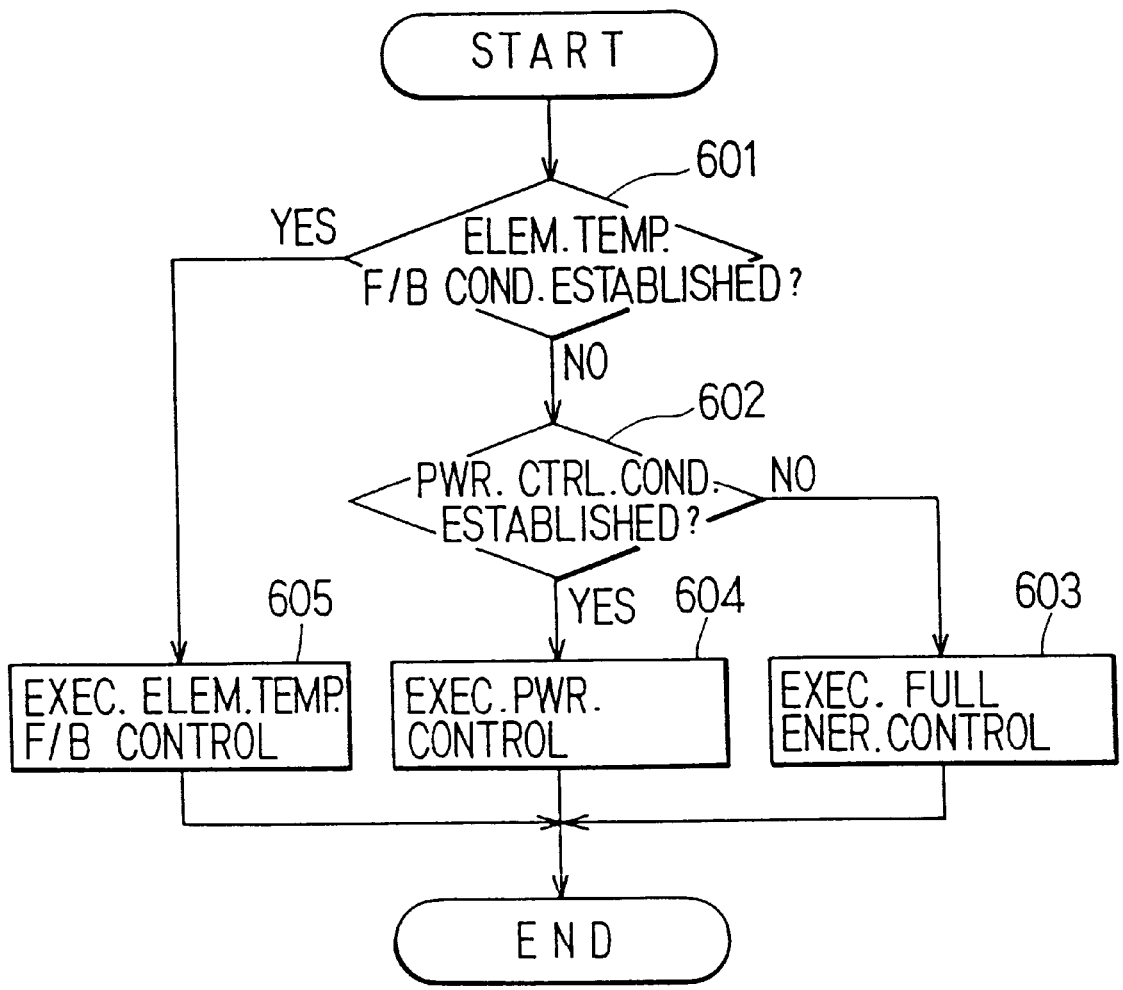
FIG. 13 is a flowchart illustrating a heater control routine according to the third embodiment.

In step 601 in FIG. 13, the CPU 48a determines whether the precondition for the element temperature feedback control have been established. The precondition is satisfied if the element resistance of the oxygen sensor 26 is equal to or less than 30 Ω. The CPU 48a determines in step 602 whether the preconditions for the power control have been established. Two different preconditions have been arranged separately in accordance with whether the oxygen sensor 26 (the sensor body 32 and the heater 33) is in a cold state or not. If the oxygen sensor 26 is in the cold state, the precondition is satisfied when a predetermined length of time has elapsed following the starting of the full energization control (the control mode (1) indicated in FIGS. 12A–12D). If the oxygen sensor 26 is no longer in the cold state, the precondition is satisfied when the heater resistance has reached or exceeded a target heater resistance. By executing the full energization control selectively when the oxygen sensor 26 is in the cold state, an excessive rise of the heater temperature can be prevented when the engine 1 is restarted.

If both step 601 and step 602 make a negative determination in an initial period of the heater control, the CPU 48a proceeds to step 603 to execute the full energization control of the heater 33 (the control mode (1)). That is, the 100% duty heater voltage is applied to the heater 33.

If the preconditions for the power control are satisfied in step 602, the CPU 48a proceeds to step 604 to execute the power control (the control modes (2), (3)). As described above, if the element resistance is in the undetectable range (element resistance>600 Ω), the power supply to the heater 33 is controlled to a fixed value (the control mode (2)). If the element resistance becomes detectable, the power supply to the heater 33 is controlled in accordance with the element resistance to maintain the heater temperature to a target heater temperature (the control mode (3)).

If the precondition for the element temperature feedback control is satisfied in step 601 in a later period, the CPU 48a proceeds to step 605 to execute the element temperature feedback control (the control mode (4)). For this control, the CPU 48a computes a heater control duty DUTY based on equations (1)–(3):

$$DUTY = DUTY\cdot I + GP + GI \quad (1)$$

$$GP = KP \cdot (Zdc - ZdcT) \quad (2)$$

$$GI = GI + KI \cdot (Zdc - ZdcT) \quad (3)$$

where DUTY·I is an initial value of the control duty DUTY; ZdcT is a control target value (according to this embodiment, DUTY·I=20% and ZdcT=30 Ω); GP is a constant of proportionality; GI is an integral term; KP is a constant of proportionality; and KI is an integration constant (according to this embodiment, KP=4.2% and KI=0.2%). These values can be experimentally determined, and will vary in accordance with the specifications of the oxygen sensor 26.

Figure 14:
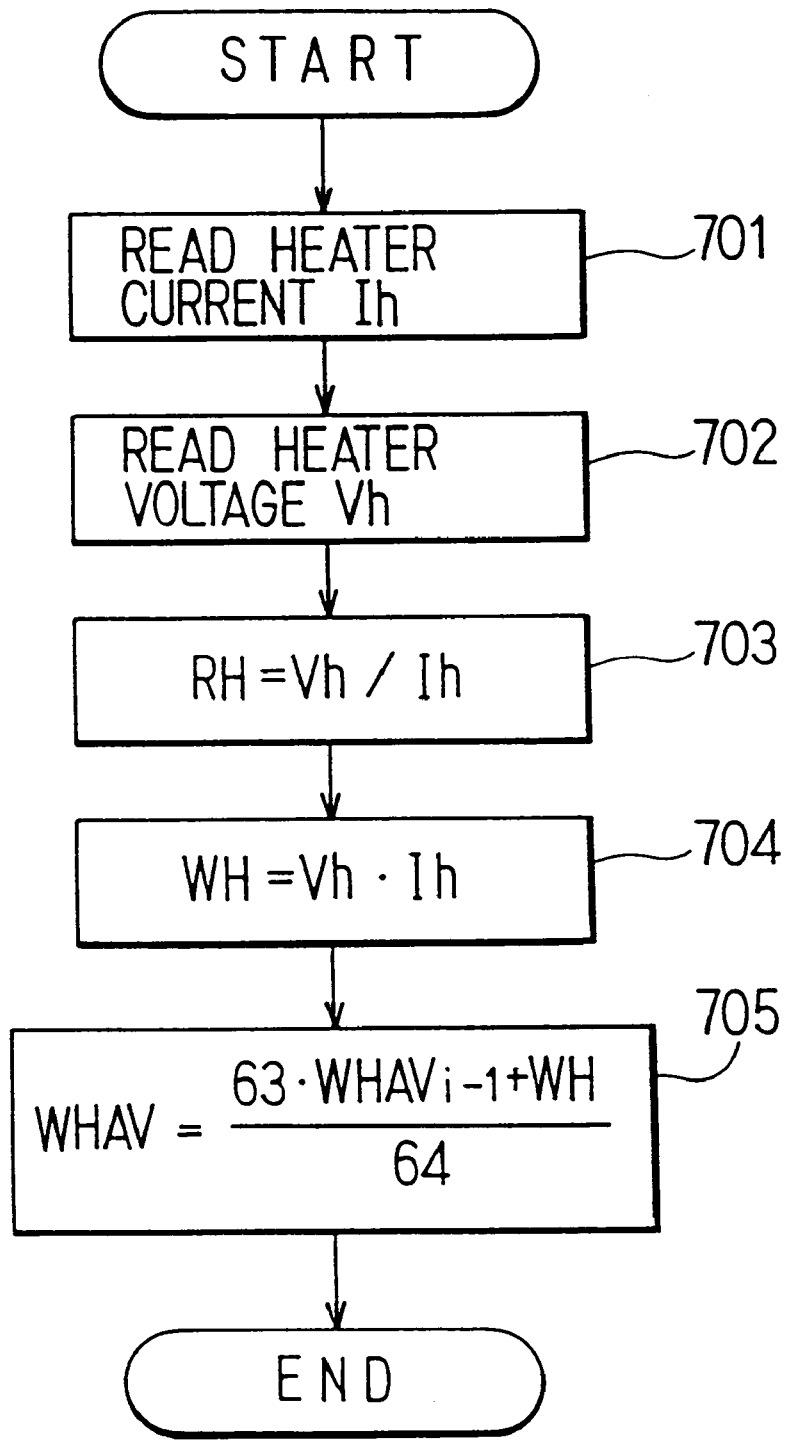
FIG. 14 is a flowchart illustrating a processed data calculating routine in the third embodiment.

The flowchart of FIG. 14 illustrating a processed data calculating routine executed by CPU 48a, for example, in a cycle of 128 ms. In step 701 in FIG. 14, the CPU 48a reads in the heater current Ih detected by the current detecting resistor 50 shown in FIG. 2. After reading in the heater voltage Vh in step 702, the CPU 48a calculates a heater resistance RH by dividing the heater voltage Vh by the heater current Ih (RH=Vh/Ih) in step 703. Step 704 multiplies the heater voltage Vh by the heater current Ih to determine the heater power supply WH (WH=Vh·Ih). Then, the CPU 48a calculates a weighted average (hereinafter, referred to as "power average WHAV") of the heater power supply WH by an averaging calculation {WHAV=(63−WHAVi−1+WH)/64}.

Figure 15:
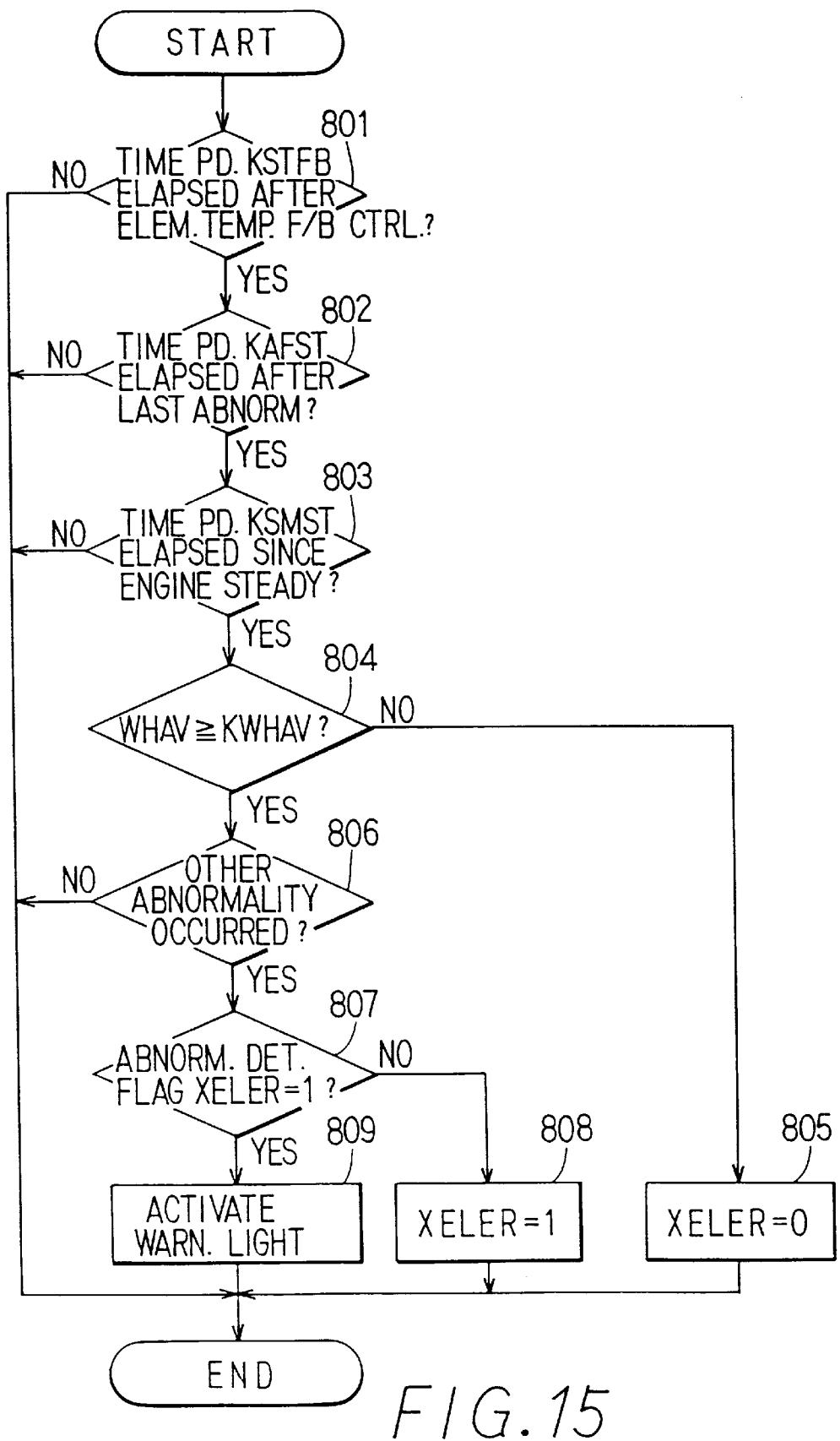
FIG. 15 is a flowchart illustrating a sensor diagnosis routine according to the third embodiment.

The flowchart of FIG. 15 illustrates a sensor diagnosis routine executed by the CPU 48a, for example, in a cycle of 1 second. The sensor diagnosis routine checks for sensor abnormality on the basis of the heater power supply WH needed during execution of the element temperature feedback control. More specifically, since the heater power supply WH needed to maintain the element temperature at a target value (for example, 700° C.) increases if the oxygen sensor 26 has abnormality, the sensor abnormality can be easily determined by comparing that heater power supply WH with the normal value. The procedure of the diagnosis will be described with reference to FIG. 15.

In step 801 in FIG. 15, the CPU 48a determines whether a predetermined length of time KSTFB (for example, 10 seconds) has elapsed following the start of the element temperature feedback control. Step 802 determines whether a predetermined length of time KAFST (for example, 100 seconds) has elapsed following the last determination of abnormality. Further, step 803 determines whether a steady engine operating state (for example, the idling state) has continued for a predetermined length of time KSMST (for example, 5 seconds). If any of steps 801–803 makes a negative determination, the CPU 48a immediately ends this routine. If all of steps 801–803 make affirmative determinations, the CPU 48a proceeds to step 804.

The CPU 48a determines in step 804 whether the power average WHAV equals or exceeds a predetermined heater power criterion KWHAV (whether WHAV≧KWHAV). If WHAV<KWHAV, it is considered that no sensor abnormality has occurred. The CPU 48a then proceeds to step 805 to clear an abnormality determination to flag XELER to "0", and then ends the routine.

On the other hand, if WHAV≧KWHAV, then the CPU 48a proceeds to step 806 to determine whether any abnormality other than sensor abnormality has been detected. If no such abnormality has been detected, the CPU 48a proceeds to step 807 to determine whether the abnormality determination flag XELER has been set to "1". If XELER=0, then the CPU 48a sets the abnormality determination flag XELER to 1 in step 808. If XELER=1, the CPU 48a proceeds to step 809 to turn on the warning light to indicate the occurrence of abnormality as a diagnosis indicating procedure. In the operation through steps 804–809, if occurrence of abnormality (WHAV≧KWHAV) is determined successively twice, the diagnosis indicating procedure is then executed.

As described above, the third embodiment feedback-controls the power supply to the heater 33 so that the element resistance (element temperature) of the oxygen sensor 26 will become a target element resistance 30 Ω (corresponding to an element temperature of 700° C.) (the element temperature feedback control illustrated in FIG. 13), and determines whether the sensor 26 is abnormal on the basis of whether the heater power supply thus controlled is greater than a predetermined abnormality determination criterion (steps 804–809 in FIG. 13). Since the element temperature feedback control will maintain the element resistance (element temperature) within a desired activation range even if sensor abnormality, such as sensor deterioration, occurs, a considerably large heater power supply is required if the oxygen sensor 26 is abnormal. Utilizing this phenomenon, the third embodiment precisely and easily detects sensor abnormalities. In addition, since the diagnosis operation is performed only during steady operation of the engine 1 (step 803 in FIG. 15), this embodiment avoids adverse effects of the exhaust gas temperature on the heater power supply and therefore performs accurate diagnosis.

Fourth Embodiment

A fourth embodiment will be described. The fourth embodiment performs diagnosis modified from the diagnosis according to the third embodiment. The flowchart of FIG. 16 illustrates a sensor diagnosis routine according to the fourth embodiment.

Figure 17:
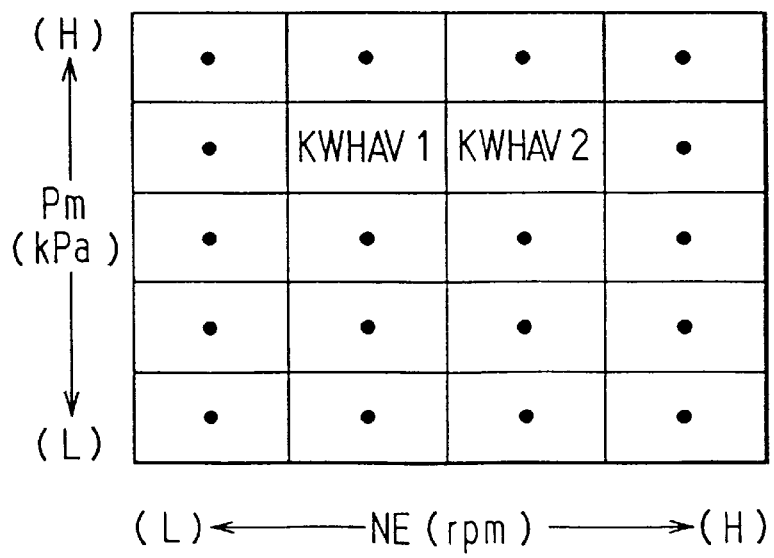
FIG. 17 illustrates a map for retrieving a heater power criterion according to the fourth embodiment.
Figure 16:
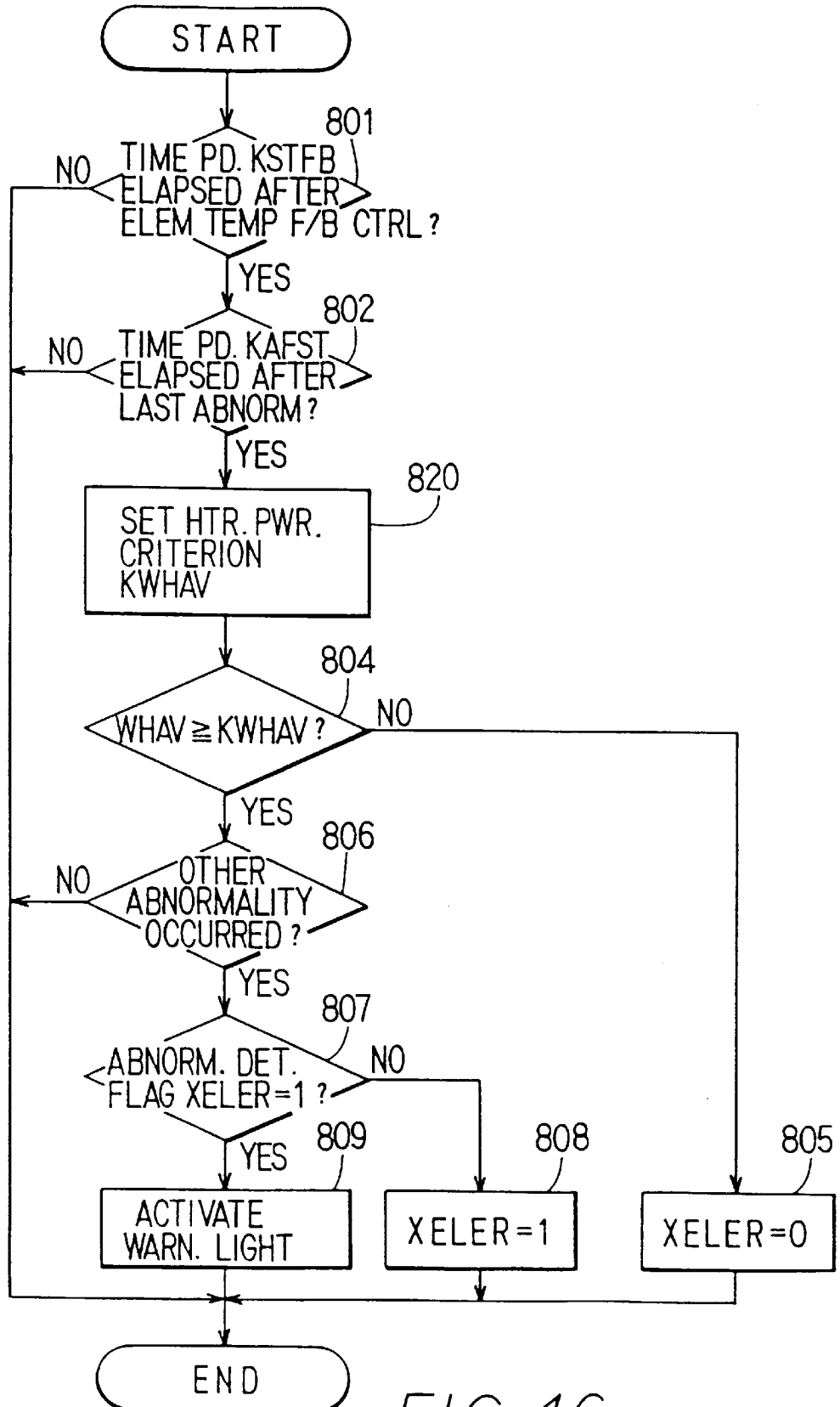
FIG. 16 is a flowchart illustrating a sensor diagnosis routine according to a fourth embodiment.

The routine illustrated in FIG. 16 executes step 820 in place of 803 in FIG. 15. Step 820 sets a heater power criterion KWHAV in accordance with the engine operating conditions. The heater power criterion WHAV is determined by using a map shown in FIG. 17. That is, the criterion WHAV is determined (for example, to KWHAV1 or KTAHAV2 as shown in FIG. 17) on the basis of the current engine speed NE and engine load (intake negative pressure Pm or intake air flow GN). The map has been arranged so that the heater power criterion KWHAV decreases as the engine speed and/or the engine load increases, and so that the heater power criterion KWHAV increases as the engine speed and/or the engine load decreases. Thus, the fourth embodiment is able to perform optimal diagnosis operation in accordance with the engine operating conditions.

Fifth Embodiment

A fifth embodiment will be described. According to this embodiment, the CPU 48a provided in the microcomputer 48 constitutes the power accumulation calculating means, the heater initial resistance detecting means, and the sensor diagnostic means.

The timing charts shown in FIGS. 18A–18E indicate heater control according to the fifth embodiment. More precisely, the timing chart indicates the operation of the heater control performed following the starting of energization of the heater 33 in response to the starting of the engine 1 until sufficient activation of the oxygen sensor 26. According to this embodiment, the heater control can be divided into four modes (1)–(3) (that is, (1) full energization control, (2) power control, and (3) element temperature feedback control) as indicated in FIGS. 18A–18E, in view of their different purposes and control methods. These control modes will be described in sequence.

In full energization control (the control mode (1)) performed immediately after the starting of the engine 1, the 100% duty heater voltage is applied to the heater 33. That is, the maximum voltage is supplied to the heater 33 to quickly heat the heater 33 when the heater 33 and the sensor element are cold. The power control (the control modes (2)) controls the power supply to the heater 33 to maintain the heater temperature at a target heater temperature (for example, 1200° C., that is, the upper limit heater temperature). The element temperature feedback control (the control mode (3)) feedback-controls the power supply to the heater 33 to achieve an element resistance of 30 Ω (corresponding to an element temperature of 700° C.) in order to maintain the activation of the sensor element. If the power supply to the heater 33 exceeds an upper limit during the element temperature feedback control, the power supply to the heater 33 is regulated.

Figure 19A:
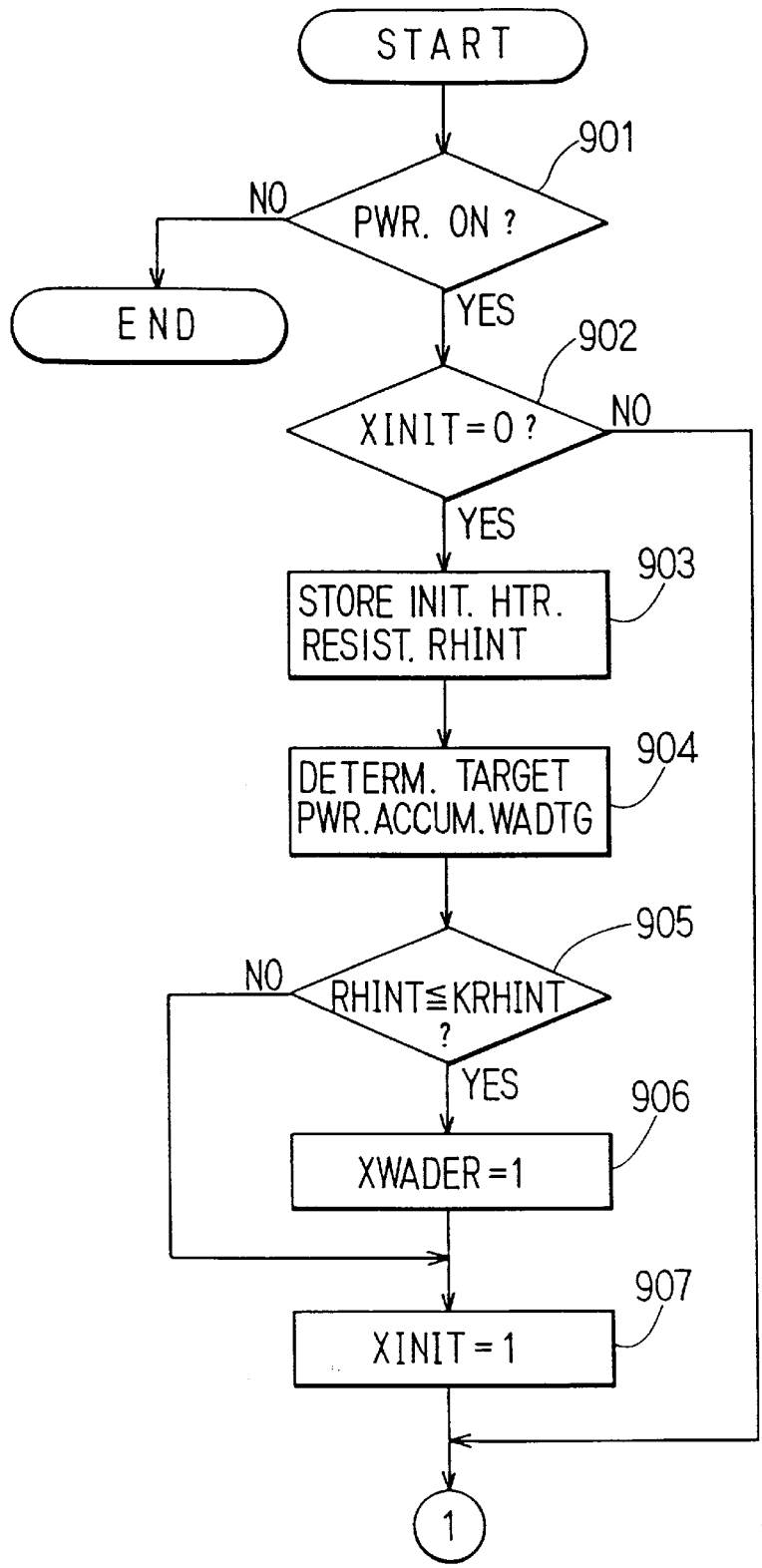
Figure 19B:
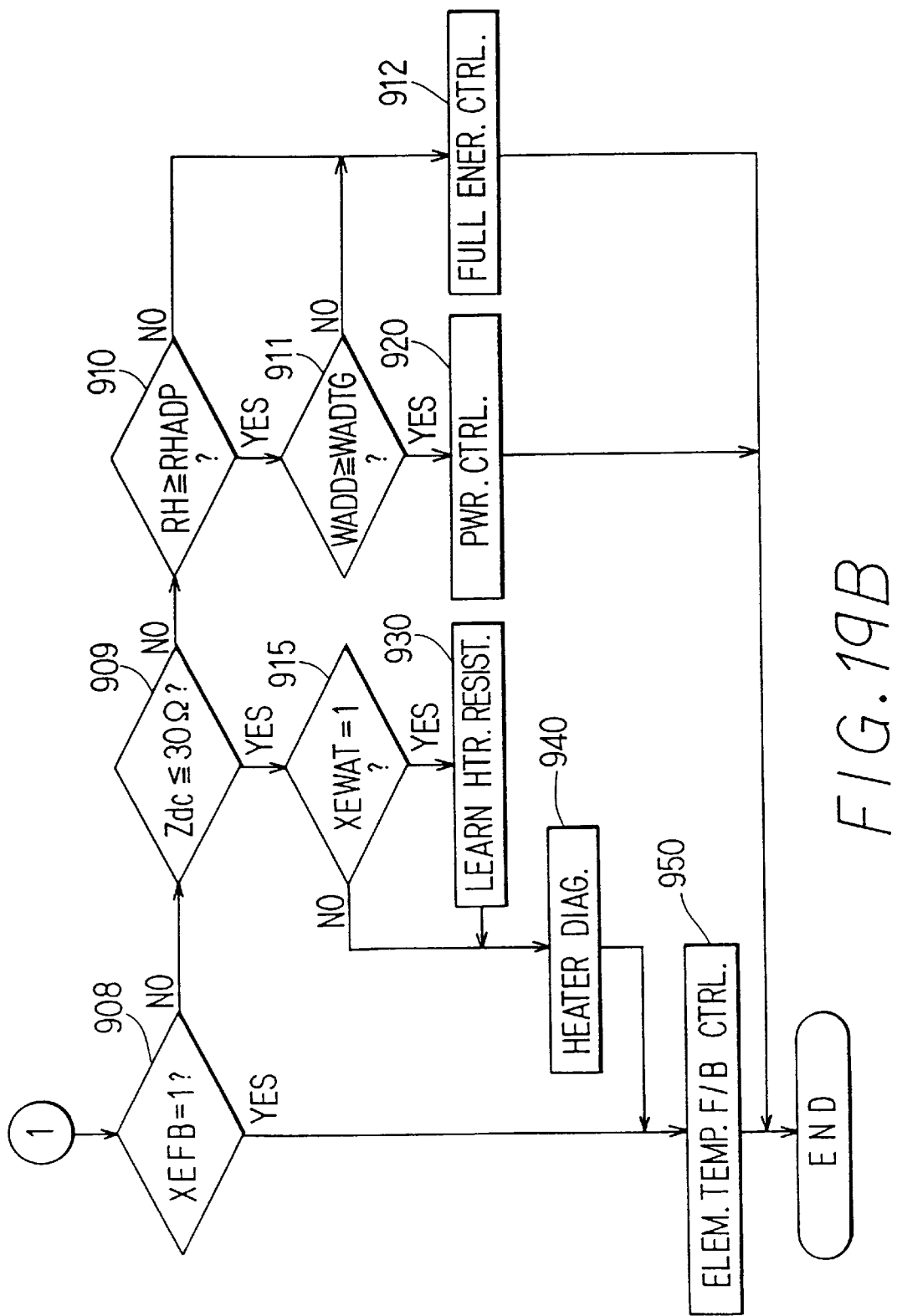

The flowchart shown in FIGS. 19A and 19B illustrates a heater control routine executed by the CPU 48a, for example, in a cycle of 128 ms. The heater control and the diagnosis operation will be described with reference to this flowchart.

In step 901 in FIG. 19A, the CPU 48a determines whether the ignition switch 28 has been turned on (whether the power is on). If the power is off, the CPU 48a ends the routine. If the power is on, the CPU 48a proceeds to step 902 to determine whether an initialization flag XINIT is "0" (the initialization flag XINIT is initialized to "0" when the power is switched on). If XINIT=0, the CPU 48a proceeds to step 903. If XINIT=1, the CPU 48a proceeds to step 908.

Figure 20:
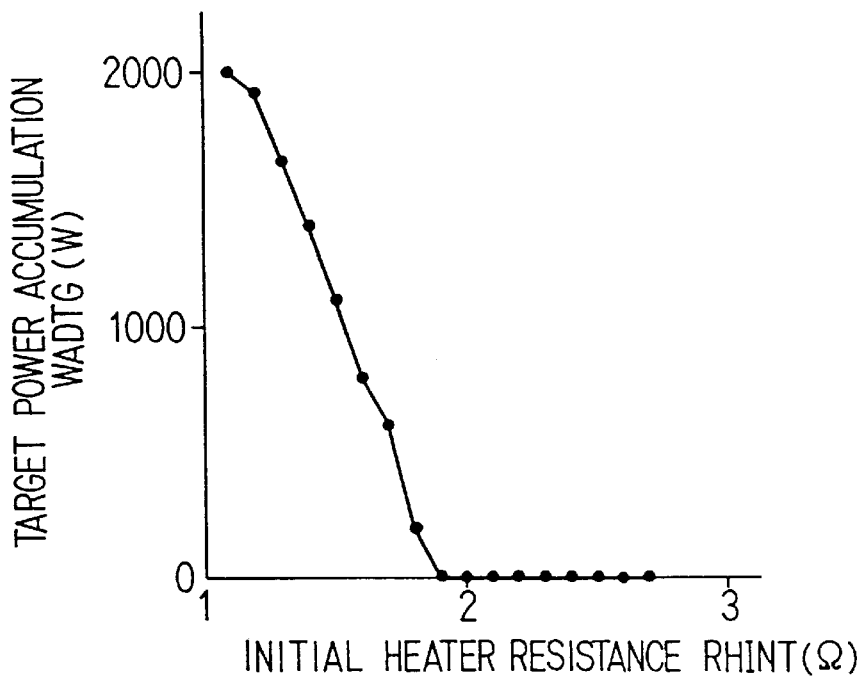
FIG. 20 is a graph indicating the relationship between the initial heater resistance and the accumulation of target power in the fifth embodiment.

Then, the CPU 48a stores the heater resistance RH determined on the basis of the heater current Ih and the heater voltage Vh (RH=VH/Ih) as an initial heater resistance RHINT in step 903. Step 904 then determines a target power accumulation WADTG based on the initial heater resistance RHINT in accordance with the relationship indicated in FIG. 20. Step 905 determines whether the initial heater resistance RHINT is equal to or less than a criterion KRHINT for determining a semi-activated state of the oxygen sensor 26. If RHINT≦KRHINT, the CPU 48*a* sets a diagnosis permission flag XWADER to "1" in step 906.

Then, the CPU 48*a* sets the initialization flag XINIT to "1" in step 907 and then proceeds to step 908. Once a target power accumulation WADTG is requested and determined after the turning-on of the power, then step 902 make negative determination and the operation will immediately proceed to step 908.

In step 908, the CPU 48*a* determines whether an element temperature feedback control flag XEFB is "1". In an initial period of the heater control (prior to a time point t1 indicated in FIGS. 18A–18E), the element temperature feedback control flag XEFB=0 and thus step 909 makes negative determination. The CPU 48*a* then proceeds to step 909 to determine whether the element resistance Zdc of the oxygen sensor 26 is equal to or less than 30 Ω (corresponding to an element temperature of 700° C.) corresponding to the temperature for performing the element temperature feedback control. If the element resistance Zdc is 30 Ω or less, the CPU 48*a* proceeds to step 915. On the other hand, if the element resistance Zdc is greater than 30 Ω, the CPU 48*a* proceeds to step 910.

The CPU 48*a* determines in step 910 whether the current heater resistance RH equals or exceeds a learned heater resistance RHADP. The learned heater resistance RHADP has been obtained by learning values of heater resistance at a target heater temperature (for example, 1200° C.) used for the power control to eliminate the effect of variations of the heater resistance caused by individual product differences or changes over time. The CPU 48*a* determines in step 911 whether a power accumulation WADD equals or exceeds the target power accumulation WADTG (value determined in step 904). The power accumulation WADD is determined by a calculation routine (not shown), for example, by successively accumulating a heater power supply WH (=Vh·Ih) detected every 128 ms (WADD=WADDi−1+WH).

If either step 910 or step 922 makes a negative determination (that is, RH<RHADP, or WADD<WADTG), the CPU 48*a* proceeds to step 912 to execute the full energization control (the control mode (1)). In the initial period prior to the time point t1 indicated in FIGS. 18A–18E, the CPU 48*a* proceeds through steps 908, 909, 910, (911) and 912 in that order, to apply the 100% duty heater voltage to the heater 33.

If both step 910 and step 911 make affirmative determination (that is, RH≧RHADP, and WADD≧WADTG), the CPU 48*a* proceeds to step 920 to execute the power control (the control mode (2)). In the period t1–t2 indicated in FIGS. 18A–18E, the CPU 48 proceeds through steps 908, 909, 910, 911 and 920 in that order, to control the power supply to the heater 33 in accordance with the element resistance to maintain the heater temperature to a target heater temperature. In step 920, a power control execution flag XEWAT is set to "1".

At the time point t2 indicated in FIGS. 18A–18E, the CPU 48*a* makes an affirmative determination in step 909, and then proceeds to step 915 to determine whether the power control execution flag XEWAT is "1". If XEWAT=1, the CPU 48*a* proceeds to step 930 to execute the learning of heater resistance, and then proceeds to step 940. On the other hand,
if XEWAT=0, the CPU 48*a* immediately proceeds to step 940. The heater resistance learning in step 930 determines whether the current heater resistance RH is greater than a value obtained by the following calculation: the heater resistance learned value RHADP+α % (for example, α=2%). If the current heater resistance RH is greater than that value, the heater resistance learned value RHADP is updated to the current heater resistance RH.

Then, the CPU 48*a* executes the heater diagnosis routine (described later) in step 940, and the element temperature feedback control in step 950. In this case, the CPU 48*a* resets the power control execution flag XEWAT to "0" and sets the element temperature feedback control XEFB to "1". The CPU 48*a* determines the control duty DUTY for the heater control circuit 46 separately in three different manners (a) to (c) as follows.

(a) When the elapsed time following the turning-on of the power is a predetermined length of time (for example, 24.5 seconds) or longer, the control duty DUTY is determined on the basis of equations (4)–(7):

$$DUTY=GP+GI/16+GD \tag{4}$$

$$GP=KP\cdot(Zdc-ZdcT) \tag{5}$$

$$GI=GIi-1+KI\cdot(Zdc-ZdcT) \tag{6}$$

$$GD=KD\cdot(Zdci-Zdci-1) \tag{7}$$

where ZdcT is a control target value (according to this embodiment, DUTY·I=20% and ZdcT=30 Ω); GP is a constant of proportionality; GI is an integral term; GD is a differential term; KP is a constant of proportionality; KI is a constant of integration; and KD is a differentiation constant.

(b) If the elapsed time following the turning-on of the power is less than the predetermined length of time (for example, 24.5 seconds) and the air-fuel ratio>12, the control duty DUTY is calculated on the basis of equation (8) using the proportional term GP and the integral term GI:

$$DUTY=GP+GI/16+GD \tag{8}$$

If the elapsed time following the turning-on of the power is less than the predetermined length of time (for example, 24.5 seconds) and the air-fuel ratio≦12, the control duty DUTY is calculated on the basis of equation (9). However, in this case (air-fuel ratio≦12), the element temperature feedback control by PID is difficult and, therefore, the heater resistance feedback control is performed instead of the element temperature feedback control.

$$DUTY=HDUTYi-1+KPA\cdot(RHG-RH) \tag{9}$$

where KPA is a constant and RHG is a target heater resistance (2.1 Ω, corresponding to 1020° C.).

The heater diagnosis routine in step 940 in FIG. 19B will be described with reference to FIG. 21.

In step 941, the CPU 48*a* determines whether the diagnosis permission flag XWADER is "1". If XWADER=0, the CPU 48*a* immediately ends the routine. If XWADER=1, the CPU 48*a* proceeds to step 942 to determines whether the power accumulation WADD equals or exceeds a predetermined abnormality determination criterion KWADER (whether WADD≧KWADER). If WADD<KWADER, the CPU 48*a* proceeds to step 943 to clear an abnormality determination flag XELER to "0".

On the other hand, if WADD≧KWADER, the CPU 48*a* proceeds to step 944 to determine whether the abnormality determination flag XELER has been set to "1". In the operation through steps 944–946, if the occurrence of an abnormality is determined successively twice, the diagnosis indicating procedure is then executed (the warning light 29 is turned on).

Figure 21:
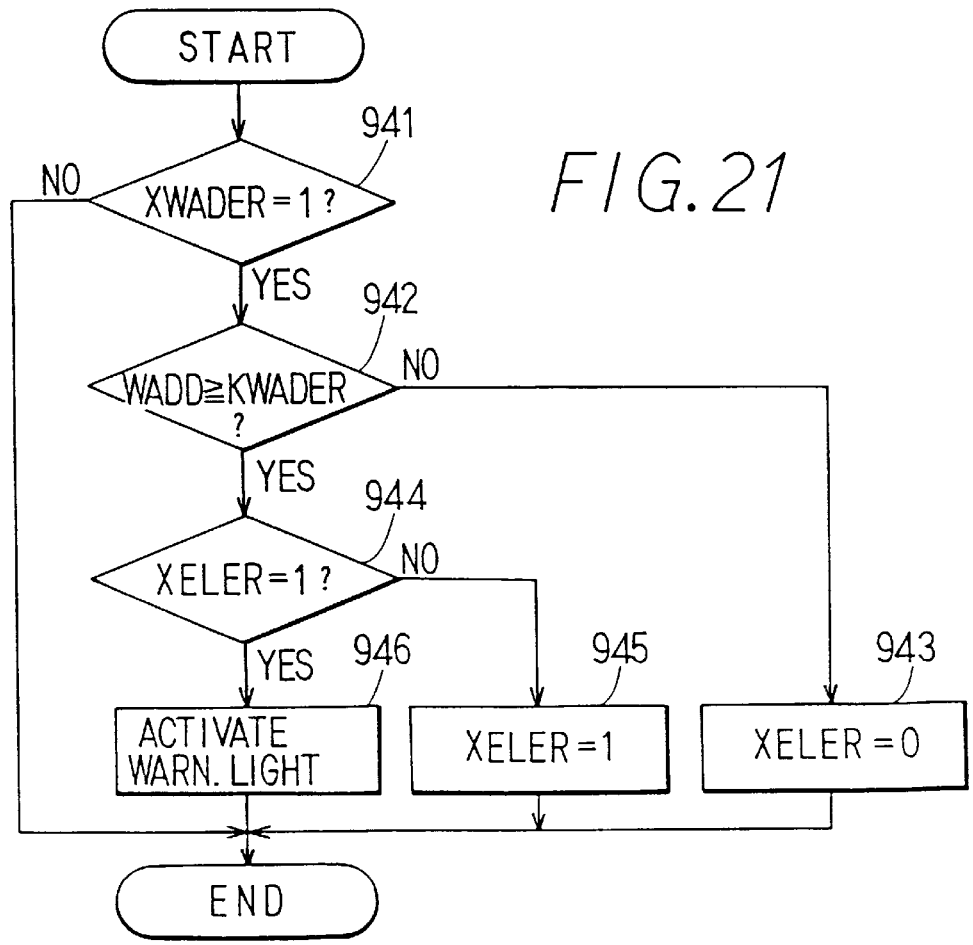
FIG. 21 is a flowchart illustrating a heater diagnosis routine according to the fifth embodiment.

As described above, the fifth embodiment calculates accumulation (power accumulation WADD) of the heater power supply from the start of energization of the heater 33, and determines whether the power accumulation WADD is greater than the predetermined abnormality determination criterion KWADER to determine whether the oxygen sensor 26 is abnormal (steps 942–946 in FIG. 21). By performing diagnosis based on the accumulation of the heater power supply, this embodiment enhances the precision of diagnosis data and thereby provides accurate diagnosis.

Moreover, the fifth embodiment detects the initial heater resistance at the start of energization of the heater 33 (step 903 in FIG. 19A) and allows the sensor diagnosis to be executed only if the initial heater resistance is within a predetermined range such that it will be determined that the oxygen sensor 26 is in a cold state (that is, Yes in step 905 in FIG. 19A). For example, when the heater energization is started in response to the restart of the engine after warming-up, the accumulation of the heater supply power is relatively small and it is not preferable to use this accumulation as a basis for the diagnosis, considering the precision of the sensor diagnosis. Therefore, this embodiment performs the diagnosis only when the oxygen sensor is in the cold state, and thus constantly provides good diagnosis.

Although the present invention has been fully described in connection with the preferred embodiment thereof with reference to the accompanying drawings, it is to be noted that various changes and modifications will become apparent to those skilled in the art. Such changes and modifications are to be understood as being included within the scope of the present invention as defined by the appended claims.

What is claimed is:

1. An oxygen concentration detecting apparatus comprising:

a limit current type oxygen sensor having an oxygen concentration detecting element for a outputting limit current proportional to oxygen concentration, and a heater for heating said detecting element;

element resistance detecting means for detecting an element resistance of said detecting element;

heater power supply control means for feedback-controlling power supply to said heater to eliminate a difference between said element resistance detected by element resistance detecting means and a target element resistance of said detecting element; and sensor diagnostic means for performing diagnosis of said oxygen sensor in accordance with whether said power supply to said heater feedback-controlled by said heater power supply control means is greater than a predetermined abnormality determination criterion.

2. An oxygen concentration detecting apparatus according to claim 1, wherein said sensor diagnostic means sets said predetermined abnormality determination criterion in accordance with operating conditions of an internal combustion engine.

3. An oxygen concentration detecting apparatus according to claim 2, wherein said sensor diagnostic means increases said predetermined abnormality determination criterion as an engine speed of said internal combustion engine decreases or as a load of said internal combustion engine decreases.

4. An oxygen concentration detecting apparatus according to claim 1, further comprising:

power accumulation calculating means for calculating an accumulation of said power supply to said heater from starting of energization of said heater;

wherein said sensor diagnostic means performs diagnosis of said oxygen sensor in accordance with whether said accumulation of said power supply to said heater calculated by said power accumulation calculating means is greater than a predetermined abnormality determination criterion.

5. An oxygen concentration detecting apparatus according to claim 1, further comprising:

initial heater resistance detecting means for detecting an initial resistance of said heater at starting of energization of said heater; and diagnosis permitting means for permitting said diagnosis by said sensor diagnostic means only if said initial resistance of said heater detected by said initial heater resistance detecting means is within a range such that it will be determined that said oxygen sensor is in a cold state.

* * * * *